United States Patent [19]
Arenburg

[11] Patent Number: 5,476,446
[45] Date of Patent: Dec. 19, 1995

[54] MULTI-FUNCTIONAL INNER EAR TREATMENT AND DIAGNOSTIC SYSTEM

[75] Inventor: Irving K. Arenburg, Englewood, Colo.

[73] Assignee: Inner Ear Medical Delivery Systems, Inc., Denver, Colo.

[21] Appl. No.: 426,190

[22] Filed: Apr. 21, 1995

Related U.S. Application Data

[62] Division of Ser. No. 138,827, Oct. 18, 1993, Pat. No. 5,421,818.

[51] Int. Cl.$^6$ ............................................. A61M 25/00
[52] U.S. Cl. ............................ 604/21; 604/20; 604/54
[58] Field of Search ......................... 604/20–21, 892.1, 604/96–103, 52–53; 128/DIG 12, 24 AA

[56] References Cited

U.S. PATENT DOCUMENTS

| | | |
|---|---|---|
| 5,282,785 | 2/1994 | Shapland et al. |
| 5,286,254 | 2/1994 | Shapland et al. |
| 5,304,134 | 4/1994 | Kras et al. |
| 5,421,818 | 6/1995 | Arenberg |

Primary Examiner—C. Fred Rosenbaum
Assistant Examiner—Perry E. Van Over
Attorney, Agent, or Firm—Klaas, Law, O'Meara & Malkin

[57] ABSTRACT

A therapeutic treatment apparatus for use in the middle and inner ear. The apparatus includes a tubular stem portion attached to a medicine-retaining reservoir with an internal cavity. The reservoir includes multiple pores therethrough or an opening having a semipermeable membrane therein which enables medicine delivery from the reservoir. Such delivery occurs when the reservoir comes in contact with selected middle-inner ear interface tissues. A conductive member for receiving electrical potentials from ear tissues is affixed to the apparatus. Alternatively, the apparatus may include tubular first and second stem portions secured on opposite sides of a reservoir along with a conductive member attached thereto of the type indicated above. This apparatus is surgically inserted so that the first stem portion is placed within the inner ear. At least part of the apparatus (the second stem portion) resides within the external auditory canal. A further alternative embodiment involves an apparatus with a stem portion, a reservoir, and an inflatable insert member therein. The insert member is operatively connected to a temperature-controlled fluid supply designed to deliver fluids (e.g. gases or liquids) to the insert causing expansion thereof. Such expansion can therapeutically modify the pressure characteristics of inner ear fluids and fluid chambers.

12 Claims, 5 Drawing Sheets

MULTI-FUNCTIONAL INNER EAR TREATMENT AND DIAGNOSTIC SYSTEM

This application is a division of application Ser. No. 08/138,827, filed Oct. 18, 1993 now U.S. Pat. No. 5,421,818.

BACKGROUND OF THE INVENTION

The present invention generally relates to an apparatus for therapeutically treating and/or analyzing conditions of the inner ear, and more particularly to a multi-functional medical apparatus for use in connection with the inner ear wherein the apparatus is capable of (1) delivering therapeutic agents to internal ear (e.g. inner ear) structures; (2) withdrawing fluid materials from the inner ear; (3) causing temperature, pressure and/or volumetric changes in the fluids and fluid chambers of the inner ear; and (4) enabling internal (e.g. inner) ear structures to be electrophysiologically monitored.

In order to treat various ear disorders, it may often be necessary to deliver therapeutic agents to inner and middle ear tissues ill a rapid and efficient manner. For example, a variety of structures have been developed which are capable of delivering/administering therapeutic agents into the external auditory canal of the outer ear. U.S. Pat. No. 4,034,759 to Haerr discloses a hollow, cylindrical tube manufactured of sponge material (e.g. dehydrated cellulose) which is inserted into the external auditory canal of a patient. When liquid medicines are placed in contact with the tube, it correspondingly expands against the walls of the auditory canal. As a result, accidental removal of the tube is prevented. Furthermore, the medicine absorbed by the tube is maintained in contact with the walls of the external auditory canal for treatment purposes. Other absorbent devices for treatment of the auditory canal and related tissue structures are disclosed in U.S. Pat. No. 3,528,419 to Joechle, U.S. Pat. No. 4,159,719 to Haerr, and U.S. Pat. No. 2,642,065 to Negri. The Negri patent specifically discloses a medicine delivery device with an internally mounted, frangible medicine container which, when broken, releases liquid medicines into an absorbent member.

However, the delivery of therapeutic agents in a controlled and effective manner is considerably more difficult with respect to tissue structures of the inner ear (e.g. those portions of the ear contained within the temporal bone which is the most dense bone tissue in the entire human body). Exemplary inner ear tissue structures of primary importance include but are not limited to the cochlea, the endolymphatic sac/duct, the vestibular labyrinth, and all of the compartments which include these components. Access to the foregoing inner ear tissue regions is typically achieved through a variety of structures, including but not limited to the round window membrane, the oval window/stapes footplate, and the annular ligament. For the purposes of this invention, these items in which access to the inner ear may be accomplished shall be considered middle-inner ear interface tissue structures as described in greater detail below. In addition, as indicated herein, the middle ear shall be defined as the physiological air-containing tissue zone behind the tympanic membrane (e.g. the ear drum) and ahead of the inner ear. It should also be noted that access to the inner ear may be accomplished through the endolymphatic sac/endolymphatic duct and the otic capsule.

The foregoing inner ear tissues are of minimal size, and only readily accessible through microsurgical procedures. In order to treat various diseases and conditions associated with these and other inner ear tissues, the delivery of medicines thereto is often of primary importance as previously noted. Exemplary medicines which are typically used to treat inner ear tissues include but are not limited to urea, mannitol, sorbitol, glycerol, xylocaine, epinephrine, immunoglobulins, sodium chloride, steroids, heparin, hyaluronidase, aminoglycoside antibiotics (streptomycin/gentamycin), and other drugs, biological materials, and pharmaceutical compositions suitable for treating tissues of the human body. Likewise, treatment of inner ear tissues and/or fluids may involve altering the pressure, volumetric, and temperature characteristics thereof. Specifically (as will be described in greater detail below), a precise balance must be maintained with respect to the pressure of various fluids within the inner ear and its associated compartments. Imbalances in the pressure levels of such fluids can cause various problems, including but not limited to conditions known as endolymphatic hydrops, endolymphatic hypertension, perilymphatic hypertension, and perilymphatic hydrops as discussed in greater detail below.

In accordance with the present invention, unique and specially-designed treatment units are disclosed which are capable of performing a wide variety of therapeutic functions including but not limited to (1) the controlled, repeatable, and sustained delivery of therapeutic agents directly into the inner ear or at selected middle-inner ear interface tissues; (2) the measurement of inner ear electrical potentials (evoked or otherwise) using a technique known as "electrocochleography" (hereinafter "ECoG") which is described in greater detail below; (3) the alteration of temperature, volume and pressure conditions within the inner ear; and (4) the controlled withdrawal of inner ear fluid materials. Accordingly, the present invention represents an advance in the art of inner ear treatment and drug delivery as described in detail below.

SUMMARY OF THE INVENTION

It is an object of the present invention to provide a multi-functional inner ear treatment and diagnostic system which enables the efficient delivery of therapeutic/diagnostic agents to selected inner ear tissues and tissue regions.

It is another object of the invention to provide a multi-functional inner ear treatment and diagnostic system wherein the foregoing therapeutic/diagnostic agents are delivered either directly into the inner ear, or through middle-inner ear interface tissues.

It is another object of the invention to provide a multi-functional inner ear treatment and diagnostic system which enables the sustained delivery of the foregoing therapeutic/diagnostic agents to selected inner ear tissues and middle-inner ear interface tissues in a controlled, repeatable, and uniform manner.

It is yet another object of the invention to provide a multi-functional inner ear treatment and diagnostic system of minimal size which is readily inserted within the inner ear or at middle-inner ear interface tissues using minimally-invasive microsurgical procedures.

It is a further object of the invention to provide a multi-functional inner ear treatment and diagnostic system which is readily supplied with additional quantities of therapeutic/diagnostic agents while the system is maintained in position within the ear of a patient.

It is an even further object of the invention to provide a multi-functional inner ear treatment and diagnostic system having a subsystem (e.g. an electrode assembly) associated therewith which is capable of delivering and receiving electrical signals (e.g. electrical potentials) to and from selected inner ear tissues, inner ear regions, and middle-inner ear interface tissues for a wide variety of therapeutic and/or diagnostic purposes.

It is an even further object of the invention to provide a multi-functional inner ear treatment system having means associated therewith for changing the temperature, volume and/or pressure levels of inner ear fluids and fluid chambers.

In accordance with the foregoing objects, the present invention involves a highly efficient and compact treatment/ diagnostic apparatus for delivering therapeutic agents to inner ear tissues and tissue regions which interface with the inner ear. The apparatus is also designed to electrophysiologically measure the effects of therapeutic agent delivery. The selected therapeutic agents may either be in liquid form, gel form, or in solid (e.g. crystalline or powder) forms which are readily hydrated within the apparatus so that a liquid product is produced on demand. The apparatus of the present invention is readily inserted in position through routine microsurgical procedures undertaken by skilled oto microsurgeons, and likewise preferably includes a conductive electrode system for receiving resting or evoked electrical potentials from the inner ear so that they may be analyzed. Such potentials are typically associated with electrocochleography ("ECog") procedures as described in greater detail below. The conductive electrode system described herein may also be used to deliver electrical waveforms to the inner ear and to selected middle-inner ear interface tissues.

In a first embodiment of the invention, a multi-functional treatment/diagnostic apparatus is provided which consists of a body portion preferably manufactured of a resilient, flexible, and inert material. It is likewise preferred that the selected construction material used to produce the body portion be as soft and stretchable as possible, and entirely devoid of sharp edges. In an alternative embodiment, the construction material may be selected so that all or a portion of it is radiopaque (e.g. visible in X-ray images taken of the body portion). Furthermore, the body portion is optimally of unitary (e.g. single-piece) construction, although the invention described herein may likewise be constructed of multiple components joined together in a conventional manner. The body portion specifically includes a tubular stem portion having an open first end, a second end, and a passageway extending continuously through the stem portion from the first end to the second end thereof. Operatively and fixedly connected to the second end of the stem portion is a reservoir portion which, in a preferred embodiment, is spherical, ovoid, or bulb-like in configuration. The reservoir portion (which is likewise preferably of single-piece, unitary construction) is sized to receive and retain a supply of medicines or diagnostic agents therein, and further includes an exterior wall and an internal cavity therein surrounded by the wall. A number of different liquid, gel-type or solid medicines/ diagnostic agents may be received and retained within the reservoir portion including but not limited to urea, mannitol, sorbitol, glycerol, xylocaine, epinephrine, immunoglobulins, sodium chloride, steroids, heparin, hyaluronidase, and aminoglycoside antibiotics (streptomycin/gentamycin), as well as other drugs, biological materials, and pharmaceutical compositions suitable for treating and diagnosing tissues of the human body. In addition, the reservoir portion may be supplied with medicine precursor materials (e.g. medicines in solid [crystalline or powder] form) to which water or other fluids may be added for the in situ production of liquid medicine materials.

So that the selected medicines may be effectively delivered to inner ear tissues in a controlled and efficient manner, the exterior wall of the reservoir portion includes fluid transfer means therein for enabling the passage of fluid materials (e.g. liquid medicines) therethrough. In a preferred embodiment, the fluid transfer means will consist of a section of the wall which is suitably fenestrated. The term "fenestrated" as used herein shall involve a section of the foregoing wall which includes a plurality of pores therethrough which enable fluid flow through the wall on demand as described in greater detail below. In an alternative embodiment, the fluid transfer means will involve a portion of the wall having an opening therethrough. Positioned within the opening and fixedly secured therein is a semipermeable membrane system as described in greater detail below which selectively permits fluid flow out of the reservoir portion for delivery to inner ear tissues or selected middle-inner ear tissue regions. Likewise, under certain circumstances to be described herein, the membrane system may permit the influx of inner ear fluids into and around the reservoir portion. These circumstances specifically involve situations in which chemical agents (e.g. mannitol crystals) are used which cause an osmotic pressure gradient within the reservoir portion that is sufficient to draw inner ear fluid materials into or around the reservoir portion in accordance with standard dialysis/diuresis concepts.

In a preferred embodiment, the medicine delivery apparatus described herein further includes electrical potential transmission means (e.g. an active electrode system) fixedly secured to the body portion for receiving resting or evoked electrical potentials from the inner ear (or middle-inner ear interface tissues) and transmitting the electrical potentials therefrom. These potentials are then analyzed in accordance with a specialized process known as electrocochleography or "ECoG" (described in greater detail below). The electrical potential transmission means preferably consists of at least one elongate conductive member affixed to the outer surface of the body portion. In a preferred embodiment, the elongate conductive member comprises a conductive wire having a proximal end, a medial section, and a distal end, with the proximal end being positioned directly adjacent the fluid transfer means of the reservoir portion. As a result, the proximal end is able to come in direct contact with the tissues (e.g. middle-inner ear interface tissues) to which medicine is being delivered using the apparatus of the present invention. Optimally, the proximal end of the wire includes a conductive spherical member or club/hook-like portion fixedly secured thereto (e.g. formed as an integral part thereof). The distal end of the wire is operatively connected to an external monitoring apparatus designed to analyze and interpret electrical potentials received from the foregoing ear tissues which may be generated in response to clicks, tone-bursts, pips or other sounds produced in accordance with standard ECoG procedures.

In order to use the multi-functional treatment apparatus of the present invention, the apparatus is surgically inserted and positioned within the middle ear of a patient so that the fluid transfer means of the reservoir portion is in direct physical contact with a selected middle-inner ear interface tissue structure. Surgical insertion and placement in this manner is normally accomplished via an incision in the tympanic membrane which is undertaken using standard tympanotomy procedures. Alternatively, insertion and placement of the apparatus may be accomplished using a standard tympanomeatal flap incision which likewise provides access to the middle ear and structures thereof. An exemplary and preferred middle-inner ear interface tissue structure suitable for the purposes set forth herein is the round window membrane, which is a thin, membranous structure through which liquids may diffuse in multiple directions. In addition, the apparatus of the present invention is preferably oriented so that at least a section of the stem portion (e.g. the open first end) extends through the incised tympanic membrane (or under the foregoing tympanomeatal flap), and resides within the external auditory canal of the patient.

The apparatus described herein is either pre-filled with a selected liquid medicine prior to insertion, or may be filled after insertion using a conventional syringe/needle assembly wherein the needle is inserted into the external auditory canal of the patient, and into the open first end of the stem portion of the medicine delivery apparatus. The liquid medicine is then delivered from the syringe into the stem portion, thereby filling the reservoir portion. Alternatively, the reservoir portion of the apparatus may be pre-filled with solid (e.g. crystalline, gel or powder) medicine precursor materials which are thereafter combined with water or other fluids (using the above-described conventional syringe assembly) to produce a supply of liquid medicine on demand within the reservoir. In addition, other systems instead of the foregoing syringe unit may be used to deliver liquid materials to the reservoir portion of the medicine delivery apparatus including but not limited to system known as an osmotic pump which is described in Kingma, G. G., et al., "Chronic drug infusion into the scala tympani of the guinea pig cochlea", *Journal of Neuroscience Methods*, 45:127–134 (1992). An exemplary, commercially-available osmotic pump may be obtained from the Alza Corp. of Palo Alto, Calif. (USA).

Immediately upon contact between the fluid transfer means of the reservoir portion and the selected middle-inner ear interface tissue structure (e.g. the round window membrane), liquid medicines retained within the reservoir portion are drawn osmotically or by capillary action through the exterior wall via the fluid transfer means. This situation continues until most or all of the liquid medicines are withdrawn from the reservoir portion. At that point (or after the passage of a selected time interval), the medicine delivery apparatus is either withdrawn from the patient or refilled with medicine, with the entire process thereafter being repeated. With respect to liquid medicines, refilling may be accomplished through the external auditory canal using a syringe (or other comparable system) in the same manner described above regarding the initial delivery of liquid medicines into the medicine delivery apparatus. Also, if undissolved solid (e.g. crystalline, gel, or powder) medicine precursor materials remain within the reservoir portion, further quantities of water or other liquid materials may be added thereto using the foregoing syringe or other system in order to create additional quantities of liquid medicine in situ. It should likewise be noted that the stem portion may include an optional one-way fluid control valve therein (as described in greater detail below) in order to prevent and/or control the flow of liquid medicines outwardly in a reverse direction from the reservoir portion through the stem portion.

In addition, as will be described herein, various chemical compositions may be placed within the reservoir portion which create an osmotic pressure gradient sufficient to draw liquid materials (e.g. inner ear fluids) out of the inner ear through the above-described middle-inner ear interface tissues. For example, this type of situation would result when a semi-permeable membrane is used in connection with a reservoir portion having a supply of mannitol crystals therein. Hydration of such crystals through the introduction of water (or saline solution) in the manner set forth above will create a high concentration of mannitol at the selected middle-inner ear interface tissues. As a result, an osmotic pressure gradient is produced as described above, thereby drawing inner ear fluids out of the inner ear through the selected middle-inner ear interface tissues (e.g. the round window membrane). The withdrawn inner ear fluids will then be drawn into the reservoir portion of the apparatus through the semi-permeable membrane, or will be deposited outside of the reservoir portion in various regions adjacent thereto.

To measure resting or evoked electrical potentials from selected inner ear tissues in accordance with standard ECoG procedures (described in greater detail below), the apparatus of the present invention is manipulated so that the proximal end of the conductive wire (e.g. having the spherical member or hook-like member thereon) is placed in direct contact with the middle-inner ear interface tissues of concern (e.g. the round window membrane or stapes footplate). Electrical potentials from the inner ear which are received by the foregoing interface tissue structures are then transmitted along the wire to the distal end thereof. In a preferred embodiment, the wire is sufficiently long to permit the distal end thereof to extend through the incised tympanic membrane (or tympanomeatal flap) and the external auditory canal so that the distal end terminates at a position outside of the patient's ear. The distal end of the wire is thereafter connected using standard electrical coupling components to an external monitoring apparatus designed to collect and characterize various inner ear electrical potentials in accordance with known ECoG procedures. In this manner, the apparatus of the present invention enables the controlled, effective delivery of medicine materials to selected ear tissues, and simultaneously enables inner ear electrical potentials to be efficiently measured, monitored, and analyzed. Monitoring of the foregoing electrical potentials will allow the treating physician to interpret and analyze the function/dysfunction of the inner ear in response to various changes in inner ear conditions caused by the addition of medicines, as well as induced changes in the temperature, volume, and/or pressure of fluid and tissue materials within the inner ear.

In an alternative embodiment of the invention, the treatment apparatus of the present invention again includes a body portion preferably of unitary (e.g. single-piece) construction which is manufactured from a resilient, elastic, and inert material of the same type set forth above. Again, this material should be as soft and stretchable as possible, with all or part of the body portion being radiopaque. The body portion includes a tubular first stem portion having an open first end, a second end, and a passageway extending continuously through the first stem portion from the open first end to the second end. Operatively and fixedly connected to the second end of the first stem portion is a reservoir portion which, in a preferred embodiment, is again spherical, ovoid, or bulb-like in configuration. The reservoir portion is sized to receive and retain a supply of medicines or diagnostic agents therein (e.g. in liquid, gel, or solid [crystalline or powder] form as noted above), and further includes an exterior wall and an internal cavity therein surrounded by the wall. Once again, a number of different medicine materials/diagnostic agents may be received and retained within the reservoir portion including but not limited to the compositions listed above.

The body portion of the medicine delivery apparatus further includes a tubular second stem portion substantially identical in construction and configuration to the first stem portion, although it is preferred that the second stem portion be slightly longer than the first stem portion. The second stem portion includes an open first end, a second end, and a passageway extending continuously through the second stem portion from the open first end to the second end. The second end of the second stem portion is operatively and fixedly connected to the reservoir portion. In a preferred embodiment, the first stem portion is positioned on a first side of the reservoir portion, while the second stem portion is positioned on a second side of the reservoir portion. Optimally, the first side of the reservoir portion is directly opposite the second side of the reservoir portion so that, in a preferred embodiment, the first and second stem portions are on opposite sides of the reservoir portion and in axial alignment with each other. In addition, at least one of the first and second stem portions may optionally include at least one fluid flow control valve of conventional construction therein at one of several pre-selected locations so that the directional flow of fluids therethrough may be precisely controlled.

The foregoing alternative embodiment of the medicine delivery apparatus likewise preferably includes electrical potential transmission means fixedly secured to the exterior surface of the body portion for receiving resting or evoked electrical potentials from selected inner ear tissues. These potentials are then transmitted out of the inner ear for the detection and analysis thereof in accordance with standard ECoG procedures as indicated above. In a preferred embodiment, the electrical potential transmission means again involves an elongate conductive member affixed to the exterior surface of the body portion. The conductive member preferably consists of an elongate conductive wire which includes a proximal end, a medial section, and a distal end, with the proximal end being positioned adjacent the second end of the first stem portion (e.g. at the juncture between the first stem portion and the reservoir portion). Alternatively, the proximal end of the conductive wire may be positioned adjacent the open first end of the first stem portion. As a result, the proximal end is able to come in direct contact with the ear tissues of concern as described below. Optimally, the proximal end of the wire includes a conductive spherical member or club/hook-like member fixedly secured thereto (e.g. integrally formed thereon) as indicated above. The distal end of the wire is operatively connected to an external monitoring apparatus designed to analyze and interpret electrical potentials (e.g. ECoG potentials) received from inner ear tissues and/or middle-inner ear interface tissues.

In order to use the foregoing alternative embodiment of the apparatus described above, it is surgically inserted within the middle ear (e.g. so that the reservoir portion is entirely positioned within the middle ear). Surgical insertion in this manner is preferably accomplished through an incision in the tympanic membrane using conventional surgical tympanotomy procedures or alternatively through the use of a tympanomeatal flap procedure as described above. Thereafter, using standard microsurgical techniques, the first stem portion is inserted through a previously-selected middle-inner ear interface tissue structure. In a preferred embodiment, the first stem portion is positioned through a discrete opening formed through the stapes footplate (and underlying oval window) or through the cochlear/vestibular otic capsule bone. This opening (formed using laser energy or microdrill techniques) provides access from the middle ear and/or mastoid space into any or all of the various inner ear compartments for the direct placement of the first stem portion therein. As a result, the open first end of the first stem portion is positioned adjacent to and in direct contact with the inner ear fluids (e.g. endolymph and/or perilymph), tissues, compartments, and/or tissue regions to be treated. It should also be noted that the body portion of the foregoing alternative medicine delivery apparatus is suitably positioned so that at least a section of the second stem portion (e.g. the open first end thereof) passes through the incised tympanic membrane (or beneath the foregoing tympanomeatal flap), and resides within the external auditory canal of the ear.

As stated above relative to the first embodiment of the medicine delivery apparatus, the foregoing alternative apparatus is either pre-filled with a selected liquid, gel, or solid medicine (e.g. crystals or powder) prior to insertion, or may be filled with liquid medicine after insertion using a conventional syringe/needle apparatus wherein the needle is inserted into the external auditory canal of the patient, and thereafter into the open first end of the second stem portion. The liquid medicine is then delivered from the syringe into the second stem portion, thereby filling the reservoir portion and (in a preferred embodiment), most or all of the first stem portion. An osmotic pump system as previously described may also be used instead of the foregoing syringe.

Alternatively, as noted above, the reservoir portion of the apparatus may be pre-filled with gel or solid (e.g. crystalline or powder) medicine materials which are thereafter combined with water or other solvating fluids (using the above-described conventional syringe assembly) to produce a supply of liquid medicine in situ within the reservoir portion on demand.

In order to effectively use the foregoing alternative embodiment of the medicine delivery apparatus, the open first end of the first stem portion is positioned against and/or in direct contact with the inner ear fluids, fluid compartments, tissues or tissue regions to be treated. Immediately upon such contact, liquid medicines within the first stem portion and the reservoir portion are drawn outwardly therefrom by capillary action or osmotic forces so that they are effectively applied/delivered to the tissues, compartments, or tissue regions of concern. This action continues until most or all of the medicine is withdrawn from the reservoir portion. At that point (or after the passage of a selected time interval), the medicine delivery apparatus is either refilled with liquid medicine or withdrawn from the patient (surgically or by extraction through the incised tympanic membrane and external auditory canal). As noted above, refilling of the medicine delivery apparatus with liquid medicines may be accomplished through the external auditory canal using a needle assembly (or other comparable system) in the same manner previously described regarding the initial delivery of liquid medicines into the medicine delivery apparatus. Also, if undissolved gel or solid (e.g. crystalline or powder) medicine precursor materials remain within the reservoir portion, further quantities of water or other hydrating liquids may be added thereto using the foregoing syringe or other system in order to create additional quantities of liquid medicine in situ for the continued delivery thereof.

To measure resting or evoked electrical potentials from selected inner ear tissues in accordance with standard ECoG procedures (set forth below), the present alternative embodiment of the invention is manipulated (if necessary) so that the proximal end of the conductive member (e.g. the proximal end of the wire having the foregoing spherical member or hook-like member thereon) is positioned against and in direct contact with the selected tissue structures of concern (e.g. the stapes footplate). Electrical potentials which pass through such tissue structures from the inner ear are then transmitted along the wire to the distal end thereof. In a preferred embodiment, the wire is sufficiently long to permit the distal end thereof to extend through the incised tympanic membrane (or beneath the tympanomeatal flap) and through the external auditory canal so that the distal end again terminates at a position outside of the patient's ear. The distal end of the wire is thereafter connected to an external monitoring apparatus designed to collect and characterize inner ear electrical potentials in accordance with known ECoG procedures.

In a still further alternative embodiment of the present invention, means are provided wherein changes in inner ear fluid pressure, temperature, and/or volume levels may be accomplished. As previously indicated, a precise balance exists with respect to the fluids of the inner ear (e.g. the endolymph and the perilymph). These fluids reside within discrete tissue structures, with the endolymph being retained in the membranous endolymphatic system and the perilymph being held in the membranous perilymphatic system. Such fluids are maintained within a precise balance relative to each other. If this balance does not exist, numerous problems may result. For example, if the endolymphatic fluid pressure exceeds the perilymphatic fluid pressure in the inner ear for any reason, conditions known as endolymphatic hypertension and endolymphatic hydrops can result. In a patient, endolymphatic hydrops is manifested on a clinical basis by some or all of the following conditions: episodic vertigo, sensations of fullness/pressure in the ear, fluctuating sensory hearing, and ear noise (e.g. tinnitus). Endolymphatic hydrops is the underlying physiological cause of a clinical condition known as "Meniere's Disease". In contrast, if the perilymphatic fluid pressure within the inner ear exceeds the endolymphatic fluid pressure, perilymphatic hypertension will result.

Tests and studies have shown that the application of pressure to the inner ear from selected regions within the middle ear will result in temporary or permanent changes in the pressure balance of endolymph and perilymph relative to each other. These changes have been measured electrophysiologically using standard ECoG techniques as described above. In the present invention, means are provided wherein pressure changes relative to the foregoing fluids may be accomplished in a minimally invasive manner. As described below, these changes are undertaken by the direct application of physical pressure to selected tissue structures, with such physical pressure being transmitted directly to the foregoing fluids. Alternatively, changes in fluid pressure may be accomplished by increasing or decreasing the temperature of such fluids which causes corresponding changes in fluid volume and pressure levels. For example, an increase in fluid temperature will result in a thermal expansion of the fluid, thereby increasing its volume and pressure in accordance with known physical relationships involving the pressure, temperature, and volume of fluid materials.

To specifically achieve the foregoing changes in inner ear fluid temperature, pressure, and volume levels, a modified multi-component treatment system is provided. Specifically, this system first includes a primary treatment apparatus of substantially the same type described above with respect to the first embodiment of the present invention. The primary treatment apparatus comprises a body portion having a reservoir portion and an elongate stem portion extending outwardly therefrom. The stem portion includes an open first end and a second end attached to the reservoir portion. The reservoir portion has the same characteristics set forth above (including an internal cavity therein), and further preferably includes fluid transfer means of the same type previously described (e.g. a plurality of pores or a semi-permeable membrane). However, in the present embodiment, the fluid transfer means may be omitted from the reservoir portion if desired. The primary treatment apparatus of the present embodiment may likewise include electrical potential transmission means (e.g. a conductive wire member) of the same type set forth above in the first embodiment of the invention.

The distinguishing characteristic of this embodiment of the invention involves the use of an inflatable insert member which is positioned within the body portion of the primary treatment apparatus. The insert member includes a spherical, ovoid, or bulb-like fluid receiving portion with an exterior wall and an internal chamber surrounded by the wall. However, it is important to note that the fluid receiving portion does not include fluid transfer means therein (e.g. pores, membranes, or the like). The insert member is designed for receipt within the body portion of the primary treatment apparatus as noted above. The fluid receiving portion (in a deflated condition) is smaller in size than the reservoir portion of the primary treatment apparatus, and therefore will not block the fluid transfer means in the primary treatment apparatus when the delivery of medicine therefrom is desired. However, it is preferred that the fluid receiving portion of the insert member be configured in substantially the same shape as the internal cavity of the reservoir portion in the primary treatment apparatus so that the fluid receiving portion will conform therewith when inflated with gases or liquids.

The fluid receiving portion and remaining components of the insert member are preferably manufactured of a resilient, flexible, and inert material. Once again, it is likewise preferred that the selected construction material used to produce the insert member be as soft, elastic, and stretchable as possible, and entirely devoid of sharp edges. The construction material may be selected so that all or a portion of it is radiopaque. Furthermore, the insert member is preferably of single-piece, unitary construction. However, it is preferred that the walls of the insert member be thinner than the corresponding walls of the primary treatment apparatus.

The fluid receiving portion of the insert member is fixedly connected to an elongate tubular portion which is sufficiently long so that it terminates within the external auditory canal or entirely outside of the ear. In a preferred embodiment, the tubular portion has a diameter which, in a deflated state, is sufficiently small to enable it to fit within the stem portion of the primary treatment apparatus. Likewise, the tubular portion of the insert member is preferably longer than the stem portion of the primary treatment apparatus. The tubular portion further includes an open first end (the function of which will be described hereinafter), a second end fixedly connected to the bulb-like fluid receiving portion, and a passageway extending continuously from the first end to the second end.

The primary treatment apparatus with the insert member therein is then surgically inserted and positioned within the middle ear of a patient so that the reservoir portion of the primary treatment apparatus is in direct physical contact with a selected middle-inner ear interface tissue structure. Surgical insertion and placement in this manner is normally accomplished via an incision in the tympanic membrane which is undertaken using standard tympanotomy procedures. Alternatively, insertion and placement of the apparatus may be accomplished using a standard tympanomeatal flap incision which likewise provides access to the middle ear and structures thereof. An exemplary and preferred middle/inner ear tissue structure suitable for the purposes set forth herein is the round window membrane. In addition, the primary treatment apparatus is preferably oriented so that at least a section of the stem portion (e.g. the open first end thereof) extends through the incised tympanic membrane (or beneath the foregoing tympanomeatal flap), and resides within the external auditory canal of the patient.

The open first end of the tubular portion associated with the insert member is then operatively connected to either an external supply of fluid (e.g. air, water, or other liquids/gases) via a conduit passing through the external auditory canal. The conduit includes a first end operatively connected to the external supply of fluid and a second end operatively connected to the open first end of the tubular portion. In order to selectively change or stabilize the temperature, pressure, and volume of inner ear fluid materials/fluid chambers, a fluid material from the external supply thereof is delivered to the insert member. Specifically, a selected gas or liquid is delivered through the foregoing conduit, through the tubular portion of the insert member, and into the fluid receiving portion thereof. The selected fluid is supplied at a pressure sufficient to cause volumetric expansion of the fluid receiving portion which is able to occur due to the stretchable materials used to produce it. As this occurs, the fluid receiving portion of the insert members fills the internal cavity of the reservoir portion in the primary treatment apparatus, and thereafter causes the reservoir portion to expand. Since the reservoir portion is positioned against a selected middle-inner ear interface tissue structure (e.g. the round window membrane), pressure is exerted against the selected structure which is transmitted to the fluid and tissue materials within the inner ear. Also, the supply of fluid materials for use in connection with this embodiment may likewise include a temperature control system for heating or cooling the selected fluid materials being delivered. The delivery of a heated gas or liquid to the fluid receiving portion of the insert member will cause a corresponding increase in the temperature of the reservoir portion of the primary treatment apparatus. This increase in temperature is then conductively transmitted from the reservoir portion into the inner ear via the selected middle-inner ear interface tissue structure. The heated inner ear fluids will thereafter expand, causing the volume and pressure characteristics of the fluids to increase. The opposite result will be achieved if cooled gases or liquids are delivered to the fluid receiving portion of the insert member. It should likewise be noted that the delivery of fluids to the insert member may be undertaken in discrete pulses if desired, or in a single, sustained infusion. Also, in addition to causing the foregoing effects on inner ear fluids/compartments, expansion of the insert member may likewise be used to physically force medicine materials from the reservoir portion of the primary treatment apparatus through the fluid transfer means (if used).

The foregoing embodiments of the multi-functional treatment apparatus of the present invention represent an advance in the art of the inner ear treatment, diagnosis, monitoring, and therapy. They enable the controlled, rapid, and effective delivery of medicines to selected middle or inner ear tissues/fluid compartments, and simultaneously enable inner ear electrical potentials to be efficiently measured and analyzed. As a result, the effects of medicine delivery on inner ear tissues may be monitored. Likewise, the temperature, pressure, and volumetric characteristics of inner ear fluids/fluid chambers may be favorably modified using the apparatus of the present invention. These benefits are accomplished with a minimal amount of microsurgery, and are achieved with a maximum degree of simplicity and effectiveness. These and other objects, features, and advantages of the invention will be described below in the following Brief Description of the Drawings and Detailed Description of Preferred Embodiments.

DETAILED DESCRIPTION OF PREFERRED EMBODIMENTS

The present invention involves a highly efficient multi-functional treatment apparatus specifically designed for use in treating and/or diagnosing the inner ear of a human subject. Specifically, the invention as described herein has numerous functional capabilities including but not limited to (1) delivering therapeutic agents into the inner ear or to middle-inner ear interface tissues; (2) withdrawing fluid materials from the inner ear; (3) causing temperature, pressure and volumetric changes in the fluids/fluid chambers of the inner ear; and (4) enabling inner ear structures to be electrophysiologically monitored.

With particular reference to FIGS. 1–5, a primary embodiment of a multi-functional treatment apparatus 10 produced in accordance with the present invention is schematically illustrated. The apparatus 10 includes a body portion 12 which, as noted above, is preferably of unitary (e.g. single-piece), molded construction. In a preferred embodiment, the body portion 12 is manufactured of a soft, resilient, stretchable (elastic), and biologically inert material. The flexibility and softness of the body portion 12 is of particular importance in order to avoid damage to delicate middle and inner ear tissues during the insertion or removal thereof, and is likewise important for other reasons as described below. Exemplary construction materials suitable for this purpose include but are not limited to medical grade silicone rubber, medical grade teflon, and a commercially-available, biodegradable gelatin-cellulose composition sold under the name Gelfilm™ which may be obtained from the Upjohn Company of Kalamazoo, Mich. (USA).

In addition, in certain instances, it may be desirable to manufacture all of part of the body portion 12 from medical grade silicone rubber impregnated with $BaSO_4$ or any other suitable materials (e.g. heavy metal compositions) having similar characteristics which will render all or part of the body portion 12 radiopaque when X-rays are applied thereto. Specifically, the term "radiopaque" signifies a condition wherein the body portion 12 will be visible in X-ray images taken of a patient having the treatment apparatus 10 inserted therein. This will enable the treating physician to accurately determine the precise location of the apparatus 10 within a patient after insertion.

Figure 1:
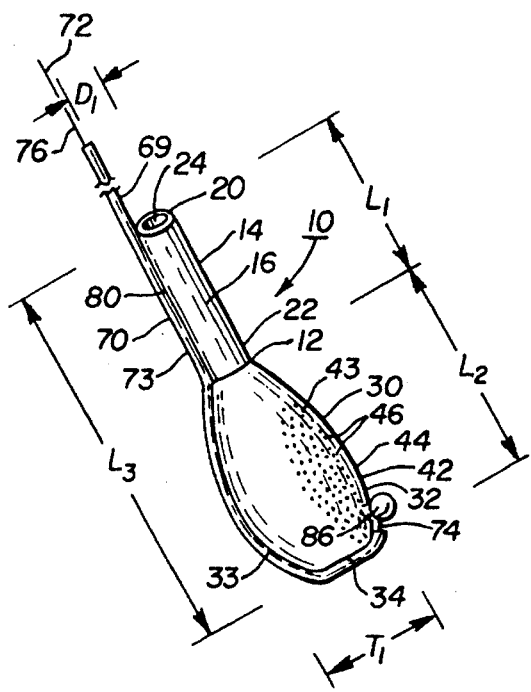
FIG. 1 is an enlarged front perspective view of a primary embodiment of a multi-functional treatment apparatus produced in accordance with the present invention for use in the human ear.
Figures 2, 3:
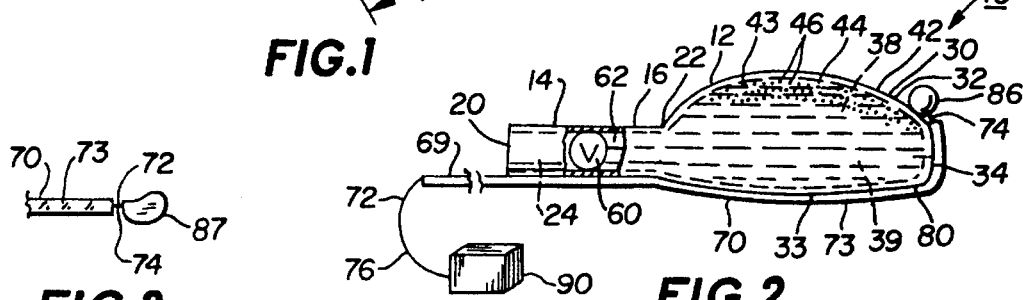
FIG. 2 is an enlarged side view of the treatment apparatus of FIG. 1 having part of the stem portion thereof broken away to show the interior thereof.
FIG. 3 is an enlarged side view of the proximal end of an alternative embodiment of the conductive wire used in connection with the treatment apparatus of FIG. 1 to receive/transmit electrical signals.

With continued reference to FIGS. 1–2, the body portion 12 further includes a tubular stem portion 14. The term "tubular" as used herein shall generally signify an elongate structure having a bore or passageway therethrough surrounded by a continuous wall. As shown in FIG. 2, the stem portion 14 includes a continuous side wall 16 which is preferably annular (e.g. circular or ring-like) in cross-section The stem portion 14 further includes an open first end 20, a second end 22, and a passageway 24 extending continuously through the stem portion 14 from the open first end 20 to the second end 22. In a preferred embodiment for use in connection with the human ear, the stem portion 14 will have a diameter "$D_1$" which is uniform along the entire length thereof from the open first end 20 to the second end 22. Optimally, for use in connection with the human ear, the diameter "$D_1$" will be about 0.2–2.0 mm. It should be noted that this diameter range (as well as other quantitative specifications and construction materials set forth herein) is for example purposes only, and the present invention shall not be limited to any particular sizes, dimensions, or physical parameters. Furthermore, the length "$L_1$" (FIG. 1) of the stem portion 14 will preferably be about 8.5–23.0 mm.

With continued reference to FIGS. 1–2, the second end 22 of the stem portion 14 is operatively and fixedly connected to an enlarged reservoir portion 30 which is designed to retain a supply of liquid, gel-type, or solid (e.g. crystalline or powdered) medicines therein. As indicated above, it is preferred the body portion 12 of the treatment apparatus 10 be of unitary (e.g. single-piece) molded construction. In this regard, the stem portion 14 and the reservoir portion 30 are, in a preferred embodiment, integrally formed together during production of the apparatus 10. Either the stem portion 14, the reservoir portion 30, or both of these components may be made radiopaque during the foregoing production process as noted above.

The reservoir portions 30 may involve numerous different external configurations. With reference to FIGS. 1–2, the reservoir portion 30 is configured in an oval (e.g. ovoid) shape with a front portion 32, a rear portion 33, and a substantially blunt end portion 34. However, the reservoir portion 30 may also resemble a sphere, bulb, or other comparable configuration. In this regard, the reservoir portion 30 of the present invention shall not be limited to any particular external shape. As illustrated in FIG. 2, the reservoir portion 30 further includes an internal cavity 38 which is adapted to receive liquid, gel-type, or solid medicines therein. An exemplary supply of liquid medicine within the internal cavity 38 is illustrated in FIG. 2 at reference number 39. Attachment of the second end 22 of the stem portion 14 to the reservoir portion 30 in the foregoing manner enables the passageway 24 in the stem portion 14 to be in fluid communication with the internal cavity 38 as illustrated in FIG. 2. While the volumetric capacity of the internal cavity 38 may be suitably varied during manufacture of the apparatus 10, it is preferred that the internal cavity 38 have a capacity of about 3.0–6.0 ml. Furthermore, as illustrated in FIG. 1, it is preferred that the reservoir portion 30 have a length "$L_2$" of about 3.0–8.8 mm, and a thickness "$T_1$" of about 2.0–8.8 mm with respect to embodiments of the apparatus 10 which are designed for use in the human ear. The overall length "$L_3$" of the body portion 12 will preferably be about 11.5–31.8 mm which will readily enable placement of the treatment apparatus 10 into the middle ear of the patient so that the apparatus 10 can contact the selected middle-inner ear interface tissues as described below.

Figure 4:
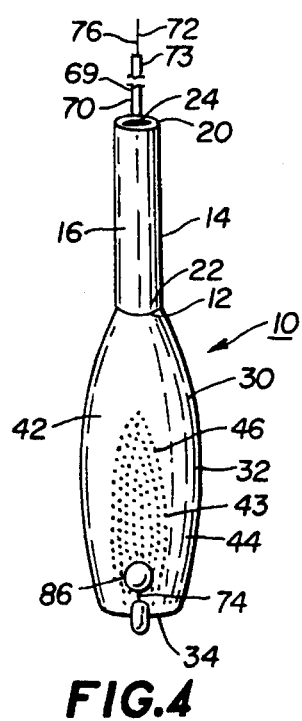
FIG. 4 is an enlarged front view of the treatment apparatus of FIG. 1 which illustrates one embodiment of the fluid transfer means associated with the reservoir portion of the apparatus.

As illustrated in FIG. 2, the internal cavity 38 of the reservoir portion 30 is surrounded by an exterior wall 42. So that medicine materials retained within the internal cavity 38 of the reservoir portion 30 may be effectively delivered to desired tissues within the middle and/or inner ear, the wall 42 includes fluid transfer means therein generally designated at reference number 43 in FIGS. 1, 2, and 4. As illustrated in FIGS. 1, 2, and 4, the fluid transfer means 43 consists of a fenestrated zone 44 which is positioned within the front portion 32 of the reservoir portion 30. The term "fenestrated" as used herein involves a portion of the wall 42 having a plurality of pores 46 (enlarged for the sake of clarity in FIGS. 1, 2 and 4) therethrough. The pores 46 enable liquid medicines to pass out of the internal cavity 38 of the reservoir portion 30 during use of the treatment apparatus 10. Also, in certain instances to be described below, the pores 46 will enable fluid materials (e.g. inner ear fluids) to be drawn into the reservoir portion 30. The size and quantity of the pores 46 may be varied during production of the apparatus 10. However, by way of example, the apparatus 10 will optimally include about 30–40 pores 46, with each pore 46 having a diameter of about 0.005–0.245 mm. The pores 46 may all be of a uniform diameter (e.g. the same size), or may involve numerous pores 46 of mixed diameters (e.g. different sizes), preferably all of which are within the foregoing diameter range. The pores 46 are specifically sized to control/minimize the spontaneous leakage of fluids (e.g. liquid medicines) outwardly from the internal cavity 38 of the reservoir portion 30. Instead, the liquid medicines will be delivered by capillary/osmotic action from the internal cavity 38 of the reservoir portion 30 when the fenestrated zone 44 of the wall 42 is placed in direct physical contact with the tissues of concern as described in greater detail below. In contrast, if solid (e.g. crystalline or powdered) or gel-type medicine precursor materials are used within the reservoir portion 30 (as described in greater detail below), such materials will not pass through the pores 46 in the reservoir portion 30 until suitably activated (e.g. solvated/hydrated) using water or other selected aqueous activator materials (saline solution and the like). As a result of such activation, and through the exertion of osmotic and capillary forces, the resulting liquid medicine materials produced in situ will then pass through the pores 46 upon contact with the selected ear tissues.

Figure 5:
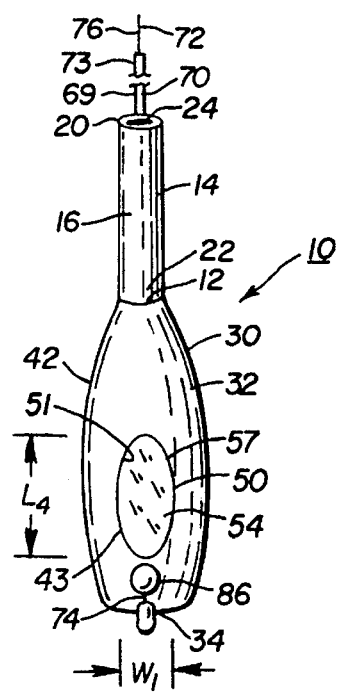
FIG. 5 is an enlarged front view of the treatment apparatus of FIG. 1 which illustrates an alternative embodiment of the fluid transfer means associated with the reservoir portion of the apparatus.

An alternative embodiment of the foregoing fluid transfer means 43 is schematically illustrated in FIG. 5. Specifically, in the embodiment of FIG. 5, the wall 42 of the reservoir portion 30 includes an opening 50 through the front portion 32. The size of the opening 50 may again be varied during production of the treatment apparatus 10, but is preferably elliptical in configuration with a length "$L_4$" of about 10–4.0 mm and a width "$W_1$" of about 1.0–6.0 mm (FIG. 5). Fixedly positioned within the opening 50 and secured to the peripheral edges 51 thereof is a semipermeable membrane 54 of a type known in the art which permits fluid to selectively flow outwardly therefrom, but will not encourage resident tissue fluids and the like to flow inwardly into the internal cavity 38 of the reservoir portion 30 unless certain circumstances are present as described below. Exemplary semi-permeable membranes suitable for use in the present invention include but are not limited to those which are known in the art and described in Kiil, F., "Molecular mechanisms of osmosis", *Am J. Physiology*, 256–260:(April 1989); Erickson, D., "The hole story, fine pore membranes remove viruses from biological drugs", *Sci. American*, vol. 267(3), pp. 163–164 Satoh, Y. et al., "The effect of inline filtration on delivery of gentamycin at various flow rates", *Keio J. Med.*, vol. 41:(1), pp. 16–22 (March 1992) which are incorporated herein by reference. Alternatively, although the use of a membrane 54 is preferred, the membrane 54 may be substituted with a micropore filter known in the art (not shown) and suitable for the purposes set forth herein. An exemplary filter for this purpose would consist of a product sold by PALL Ultrafine Filtration Co. of East Hills, N.Y. (USA) (type PALL 0.2 microns). Comparable filters are also available from Millipore, Inc. of Bedford, Mass. (USA).

Referring back to FIG. 5, the peripheral edges 57 of the membrane 54 are fixedly secured to the peripheral edges 51 of the opening 50 preferably using a conventional adhesive. Exemplary adhesives suitable for this purpose would include but not be limited to a conventional cyanoacrylate adhesive or other adhesive composition known in the art. When the membrane 54 is placed in direct physical contact with the ear tissues of concern (e.g. the selected middle-inner ear interface tissues), liquid medicines retained within the internal cavity 38 of the reservoir portion 30 will be drawn outwardly therefrom through the membrane 54 by capillary action and/or osmotic forces. The inward flow of resident tissue fluids and the like into the internal cavity 38 of the reservoir portion 30 is effectively prevented by the semi-permeable character of the membrane 54 except under special circumstances as set forth below. In addition, fluid transfer means 43 other than the examples shown in FIGS. 4–5 may be used in connection with the treatment apparatus 10 of the present invention, which shall not be exclusively limited to the embodiments set forth above.

As previously indicated, the fluid transfer means 43 (e.g. the pores 46 or membrane 54) is primarily designed to permit the controlled flow of fluid materials (e.g. liquid medicines) outwardly from the reservoir portion 30 of the apparatus 10. However, under certain circumstances, the fluid transfer means 43 will permit fluid materials to enter into the reservoir portion 30 when osmotic and other physical conditions are suitable for doing so. For example, such a situation would exist if the internal cavity 38 of the reservoir portion 30 is provided with a supply of mannitol crystals therein and a semi-permeable membrane 54 of the type described above is used. Hydration of the crystals with water will create an osmotic gradient which will draw inner ear fluids through the selected middle-inner ear tissue structures of interest (e.g. the round window membrane). These fluids will then be drawn into and/or around the reservoir portion 30. It is therefore to be understood that the fluid transfer means 43 as described herein shall not be specifically limited to the delivery of fluid materials from the reservoir portion 30 and likewise may include the withdrawal of fluid materials from the middle/inner ear into and around the reservoir portion 30 under certain circumstances.

The multi-functional treatment apparatus 10 shown in FIGS. 1–5 may further include an optional one-way fluid flow control valve 60 therein which is schematically illustrated in FIG. 2 within the passageway 24 of the stem portion 14. The valve 60 is designed to prevent the reverse flow of liquid medicines outwardly from the internal cavity 38 of the reservoir portion 30 into the stem portion 14. The valve 60 is particularly useful in embodiments of the present invention which include moderately high-capacity reservoir portions 30 with large quantities of liquid medicine therein. The valve 60 may specifically involve numerous commercially-available units, including but not limited to conventional miniature ball valves and mitre valves suitable for medical use which are known in the art, as well as a miniature slit-type valve illustrated and generally described in U.S. Pat. No. 4,175,563 to Arenberg which is incorporated herein by reference. This type of valve is commercially available from Hood Laboratories of Pembroke, Mass. (USA). The valve 60 may be retained within the passageway 24 of the stem portion 14 by conventional means, including but not limited to the use of adhesive materials (e.g. commercially-available cyanoacrylate adhesive compositions, epoxy resins, autologous fibrin glue as described in U.S. Pat. No. 4,874,368 to Miller et al. which is incorporated herein by reference, or other conventional medical grade adhesives). Alternatively, a valve 60 may be used which is sized to frictionally engage the interior surface 62 of the side wall 16 of the stem portion 14 (FIG. 2) so that the valve 60 is securely retained therein.

Finally, as illustrated in FIGS. 1–5, the treatment apparatus 10 includes electrical potential transmission means 69 fixedly secured to the body portion 12 for receiving electrical potentials from middle/inner ear tissues and transmitting them out of the ear for the detection and analysis thereof. In a preferred embodiment, the electrical potential transmission means 69 consists of an elongate conductive member 70 fixedly secured to the body portion 12 along the entire length thereof as illustrated. The elongate conductive member 70 may involve a variety of different structures. For example, it is preferred that the elongate conductive member 70 consist of a thin wire 72 (e.g. #27 gauge) manufactured from silver or a silver/silver chloride alloy. The wire 72 is preferably coated with a layer 73 of insulation thereon (FIG. 1). Exemplary insulation materials will include but not, be limited to heat shrinkable Teflon® tubing of a type well known in the art. The wire 72 further includes a proximal end 74 and a distal end 76 as illustrated. The wire 72 (surrounded by the layer 73 of insulation) is fixedly secured to the body portion 12 of the apparatus 10 in any desired or suitable position thereon. In the embodiment of FIGS. 1–5, the wire 72 is secured to the body portion 12 of the apparatus 10 along the underside 80 thereof (FIGS. 1–2). Attachment may be accomplished using a medical grade adhesive of the type set forth above cyanoacrylate, epoxy resin, or other conventional adhesive materials). Also, it should be noted that the conductive member 70 may involve other structures equivalent to the wire 72. For example, a substantially flat, flexible metallic strip (not shown) may be used in place of the wire 72, although the wire 72 is preferred.

With continued reference to FIGS. 1–2, the wire 72 preferably extends around the end portion 34 of the reservoir portion 30. In this configuration, the proximal end 74 of the conductive member 70 (e.g. wire 72) is positioned directly adjacent the reservoir portion 30 as illustrated. Specifically, in the embodiment of FIGS. 1–2, the proximal end 74 is located at a position directly adjacent the fluid transfer means 43 in the front portion 32 (e.g. adjacent the fenestrated zone 44 shown FIG. 4 or the membrane 54 of FIG. 5). In a preferred embodiment, the proximal end 74 of the wire 72 includes a conductive spherical member 86 (FIG. 1) secured thereto (e.g. integrally formed thereon). The spherical member 86 is optimally manufactured of the same material used to construct the wire 72. Use of the spherical member 86 facilitates direct contact between the wire 72 and the ear tissues of concern so that electrical potentials therefrom may be received. In an alternative embodiment as illustrated in FIG. 3, the proximal end 74 of the wire 72 may include a rounded club or hook-like portion 87 thereon instead of the spherical member 86. Thus, the proximal end 74 of the wire 72 may encompass a variety of different forms, and shall not be limited to any single structure or design. It should likewise be noted that, while the conductive member 70 (e.g. the wire 72) is primarily discussed herein as a means to receive electrical potentials, it may also be possible to use the conductive member 70 to apply electrical potentials to tissues of interest in order to measure responsive stimuli therefrom. Thus, the conductive member 70 of the present invention shall not be exclusively limited to the receipt of electrical potentials.

The distal end 76 of the wire 72 preferably extends beyond the open first end 20 of the stem portion 14 as illustrated. Upon insertion of the treatment apparatus 10 into the middle ear of a patient, the distal end 76 of the wire 72 will pass through the incised tympanic membrane (or beneath a surgically formed tympanomeatal flap as described below), through the external auditory canal of the patient, and will ultimately extend outwardly from the patient's ear. In this regard, the distal end 76 is then readily connected to an external monitoring apparatus 90 (FIG. 2) of conventional design which collects and characterizes resting or evoked electrical potentials ultimately received from the inner ear. Further information regarding the monitoring apparatus 90 will be described below.

As indicated herein, the conductive member 70 is especially designed to receive electrical potentials from selected inner ear tissues. This capability is particularly useful in connection with a process known as "ECoG" which is an abbreviation for "electrocochleography". Electrocochleography is a known technique for measuring electrical potentials from the inner ear which basically involves measurement of the whole nerve-cochlear action potential (hereinafter "AP"). Alternatively, ECoG can be used to indirectly measure hair cell electrical activity. ECoG can further be used to measure the summating potential (hereinafter "SP") within the inner ear in response to externally generated clicks, tone bursts, and/or pips. The SP is basically a D.C. distortion potential which can indicate the amount oil distortion in the cochlear duct associated with endolymphatic hydrops or other changes in the inner ear. The relative amount of distortion may be expressed either as an SP/AP ratio (in response to externally-generated clicks, etc.), or as an absolute measurement in response to specific, externally-generated tone bursts and the like. Cochlear microphonics can also be measured as well as otoacoustic emissions (hereinafter "OAE") in order to assess hair cell function or dysfunction. Finally, endocochlear potentials can be measured using the components described herein if selected portions of the conductive member 70 are operatively positioned within the cochlea rather than outside of the cochlea. Further information on ECoG is presented in Portmann, M., "Electrophysiological correlates of endolymphatic hypertension and endolymphatic hydrops: an overview of electrocochleography (ECoG)", Proceedings of the Third International Symposium and Workshops on the Surgery of the Inner Ear, Snowmass, CO (USA) Jul. 29–Aug. 4, 1990 as reported in *Inner Ear Surgery*, edited by I. Kaufman Arenberg, Kugler Publications, Amsterdam/New York, pp. 241–247 (1991) which is incorporated herein by reference.

As stated herein, the conductive member 70 (e.g. wire 72) is especially useful in connection with conventional ECoG procedures. Resting or evoked electrical potentials received by the wire 72 through direct contact of the proximal end 74 (e.g. the spherical member 86 or hook-like portion 87) with selected ear tissues are routed through the wire 72 to the distal end 76 which is operatively connected (using conventional electrical connecting clips and the like) to the monitoring apparatus 90 as stated above. An exemplary monitoring apparatus 90 suitable for use herein consists of commercially available ECoG detection systems sold under the names "Viking II™" and "Spirit™" by Nicolet, Inc. of Madison, Wis. (USA). However, a wide variety of different, commercially-available systems may be used to receive and quantify electrical potentials from the conductive member 70 (e.g. wire 72), including but not limited to computer-monitored voltage amplifier/analog-to-digital converter units known in the art. As noted above, the wire 72 is sufficiently long to enable the distal end 76 thereof to terminate at a position outside of the patient's ear. As a result, attachment of the distal end 76 of the wire 72 to the monitoring apparatus 90 is greatly facilitated. In a preferred and optimum embodiment, the total length of the wire 72 from the proximal end 74 to the distal end 76 (measured when straight) will be about 5.0 cm.

In order to use the treatment apparatus 10 as described above, the apparatus 10 is surgically inserted within the middle ear of a patient so that the reservoir portion 30 is positioned entirely within the middle ear and against a selected middle-inner ear interface tissue structure (e.g. the round window membrane). Insertion into the middle ear may be accomplished through an incision in the tympanic membrane (ear drum) or beneath a surgically formed tympanomeatal flap formed using conventional tympanotomy procedures as described in greater detail below. During insertion, the apparatus 10 is manipulated so that the fluid transfer means 43 (e.g., the fenestrated zone 44 [pores 46] or the membrane 54) is positioned against and in direct contact with the selected interface tissue structures. Furthermore, in accordance with the insertion techniques set forth herein, at least part of the stem portion 14 (e.g. the open first end 20) is positioned so that it will extend through the incised tympanic membrane or tympanomeatal flap and into the external auditory canal of the patient. When the medicine delivery apparatus 10 is positioned in this orientation, the reservoir portion 30 may be readily refilled with liquid medicines (or supplied with different medicines) through the external auditory canal and stem portion 14 without additional surgical intervention or removal of the apparatus 10. This is accomplished through the use of a conventional syringe apparatus or other comparable device as described in further detail below. Likewise, if the reservoir portion 30 includes solid (e.g. crystalline) or gel-type precursor medicine materials therein, additional liquid (e.g. water, saline solution, or the like) may be added as necessary or appropriate through the stem portion 14 and external auditory canal using the above-described syringe or other selected external fluid delivery system. In addition, the apparatus 10 is positioned/manipulated so that the proximal end 74 of the wire 72 is in direct physical contact with the interface tissue structures of concern (e.g. the round window membrane). As a result, electrical potentials may be received therefrom. This is readily accomplished through the use of wire 72 wherein the proximal end 74 (with the spherical member 86 or hook-like portion 87 thereon) is placed in direct physical contact with the selected interface tissues. Contact between the proximal end 74 of the wire 72 and the selected tissue materials is readily accomplished since the proximal end 74 is adjacent the front portion 32 of the reservoir portion 30 (e.g. adjacent the fenestrated zone 44 or membrane 54) as previously indicated.

In order to insert the medicine delivery apparatus 10 within the ear of a patient, a number of different minimally-invasive surgical techniques may be used. Accordingly, the present invention shall not be limited to the use of any specific surgical techniques. For example, as previously noted, the treatment apparatus 10 may be surgically inserted in accordance with a middle ear exploration via a tympanomeatal flap exposing the middle ear cleft and ossicular chain. The fluid transfer means 43 (e.g. the fenestrated zone 44 [pores 46] or the membrane 54) associated with the reservoir portion 30 of the medicine apparatus 10 is placed in contact with and against the round window membrane in the bony round window niche. In this orientation, the proximal end 74 (including the spherical member 86 or hook-like portion 87) of the wire 72 will likewise be in direct contact with the round window membrane. This will occur due to the close proximity of the proximal end 74 of the wire 72 with the fluid transfer means 43 as indicated above. The stem portion 14 of the apparatus 10 is then brought through the otherwise intact tympanic membrane via a tympanotomy incision in the posterior inferior portion of the tympanic membrane. The abovedescribed construction materials used to produce the apparatus 10 are sufficiently soft, flexible, and collapsible so that the entire apparatus 10 can be easily removed through the tympanotomy incision when removal of apparatus 10 is desired (e.g. normally after about 4–8 weeks). In addition, the apparatus 10 may be retained in position within the middle ear through the use of a selected adhesive applied to one or more portions of the apparatus 10. The adhesive should consist of a biocompatible material which is readily detachable from the materials adhered thereto. An exemplary adhesive suitable for this purpose involves an autologous fibrin glue as described above.

As previously stated, the treatment apparatus 10 has wide applicability in treating various inner ear tissues, tissue regions, and fluid compartments. Placement of the apparatus 10 against suitable middle-inner ear interface tissues (e.g. the round window membrane) will enable the delivered liquid medicines to pass directly therethrough and come in contact with various inner ear tissues and fluid compartments including but not limited to the cochlea, vestibular labyrinth, endolymphatic sac, endolymphatic duct, and the membranous endolymphatic/perilymphatic system. Passage of liquid materials through the round window membrane is possible in view of its minimal thickness and specific permeable physiological character. Likewise, a wide variety of liquid medicines/therapeutic agents may be used in connection with the apparatus 10, including but not limited to urea, mannitol, sorbitol, sodium chloride, steroids, heparin, hyaluronidase, aminoglycoside antibiotics (streptomycin/gentamycin), glycerol, xylocaine, immunoglobulins, and other antibiotic, biological, or antimicrobial materials. Furthermore, as previously noted, the reservoir portion 30 of the medicine delivery apparatus 10 may be initially supplied with solid (e.g. crystalline), gel-type, viscous liquid, or powdered precursor medicine materials which can be hydrated/solvated in situ in order to produce liquid medicine materials. Exemplary solid or gel-type/viscous medicine materials to which water may be added in this manner include but are not limited to mannitol crystals, sodium chloride crystals, viscous liquid glycerol, powdered streptomycin/gentamycin, hyaluronidase gel and the like. Accordingly, the present invention shall not be limited to the delivery of any specific chemical materials, biological compositions, pharmaceuticals, or therapeutic agents.

Figure 9:
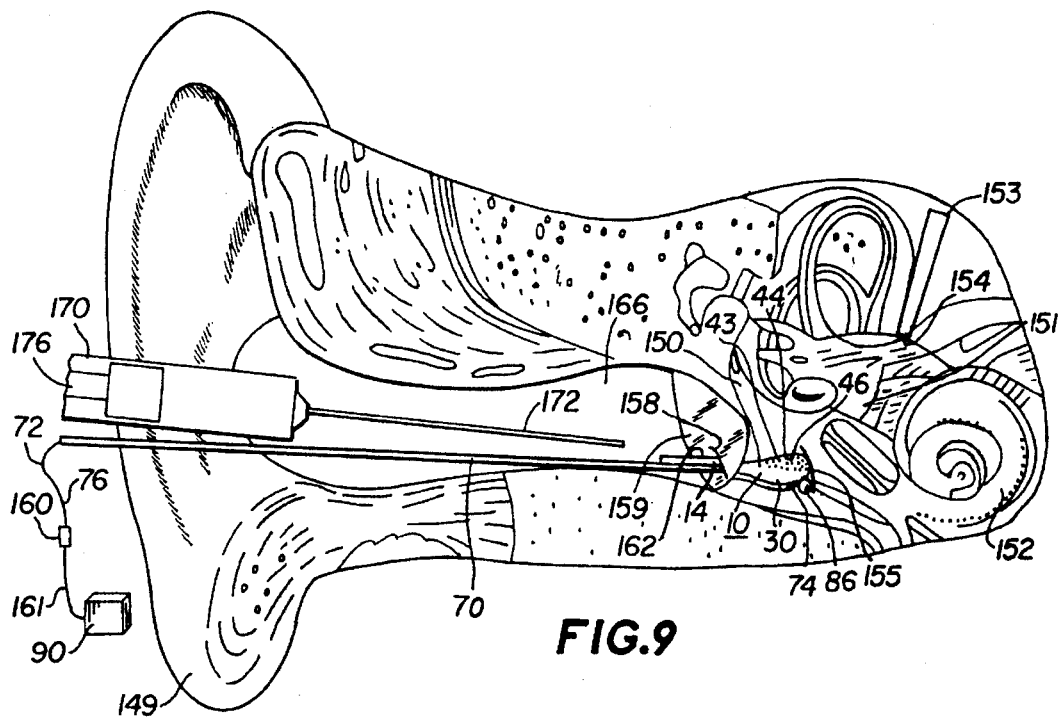
FIG. 9 is a schematic, partial cross-sectional view of the ear of a human subject illustrating the treatment apparatus of FIG. 1 inserted therein.

FIG. 9 is a schematic, partial cross-sectional view of the ear 149 of a human subject illustrating the treatment apparatus 10 of FIG. 1 inserted therein. As shown, the apparatus 10 is positioned so that the reservoir portion 30 is entirely within the middle ear, generally designated in FIG. 9 at reference number 150. The inner ear region is generally designated in FIG. 9 at reference number 151, and further includes the cochlea 152 and the endolymphatic sac 153, as well as the endolymphatic duct 154 associated therewith. The round window membrane is generally designated at reference number 155, and constitutes an interface tissue structure between the middle ear 150 and the inner ear region 151.

In FIG. 9, the reservoir portion 30 is specifically positioned so that the fluid transfer means 43 (e.g. the fenestrated zone 44) is adjacent to and in direct physical contact with the round window membrane 155 in the middle ear 150. Contact between the pores 46 of the fenestrated zone 44 and the round window membrane 155 causes liquid medicines within the internal cavity 38 of the reservoir portion 30 (FIG. 2) to be drawn by capillary action through the pores 46 and thereafter onto the round window membrane 155. The liquid medicines then diffuse through the round window membrane 155 and into the inner ear region 151 for the treatment of tissues fluids, fluid compartments, and tissue regions therein. Once again, it should be noted that the present invention shall not be limited to the treatment of any specific inner ear tissues, structures, or compartments.

Alternatively, if the embodiment of FIG. 5 were used, the semi-permeable membrane 54 (or the micropore filter structures used in connection with other embodiments) would be positioned adjacent to and in direct contact with the round window membrane 155. Direct physical contact between the membrane 54 of the reservoir portion 30 and the round window membrane 155 again causes liquid medicines within the internal cavity 38 of the reservoir portion 30 to be drawn through the membrane 54 by capillary action and/or osmotic forces. The liquid medicines subsequently come in contact with the round window membrane 155, and are then able to diffuse therethrough into the inner ear 151.

With continued reference to FIG. 9, the proximal end 74 and the spherical member 86 associated with the conductive member 70 is positioned adjacent to and in direct contact with the round window membrane 155 so that electrical potentials may be received therefrom as noted above. As previously indicated, such potentials may be produced within the inner ear 151 using externally generated tone bursts, pips and the like in accordance with standard ECoG procedures. These potentials travel through the inner ear 151 and thereafter to the round window membrane 155 where they are received by the wire 72. The distal end 76 of the wire 72 preferably passes through an incision 158 in the tympanic membrane 159, and is positioned outwardly from the ear 149 as illustrated. The distal end 76 of the wire 72 is then connected using a standard miniature connecting clip 160 to ECoG monitoring apparatus 90 via electrical conduit or wire 161. The monitoring apparatus 90 is used to analyze and quantify electrical potentials (e.g. ECoG potentials) received from the inner ear 151 in response to various stimuli or as an indication of resting potential activity.

Finally, as shown in FIG. 9, a substantial section 162 of the stem portion 14 resides within the external auditory canal 166 of the ear 149 adjacent the tympanic membrane 159 and remotely spaced from the middle ear 150. As noted above, the tympanic membrane 159 preferably has an incision 158 therein which allows the passage of both the conductive member 70 and the stem portion 14 therethrough. Alternatively, the section 162 of the stem portion 14 may pass beneath a tympanomeatal flap (not shown) depending on the techniques chosen by the surgeon. In order to supply the internal cavity 38 of the reservoir portion 30 with liquid medicines (or hydrating fluids designed to produce liquid medicines in situ), a conventional syringe 170 having a hollow needle 172 (e.g. #27 gauge) attached thereto is used. As far as liquid medicines are concerned, such materials are supplied to the internal cavity 38 of the reservoir portion 30 immediately after insertion of the treatment apparatus 10 within the ear 149, when initial supplies of liquid medicine within the reservoir portion 30 have been depleted, or when changes to previously-administered medication are necessary. Specifically, the syringe 170 is first filled with the selected liquid medicine. The needle 172 is thereafter carefully inserted into the external auditory canal 166, and into the open first end 20 of the stem portion 14. Thereafter, pressure is exerted on the plunger 176 of the syringe 170 to deliver the selected liquid medicine (or other fluid materials of interest) from the syringe 170 through the needle 172 into the stem portion 14. The liquid medicine then flows from the stem portion 14 through the valve 60 (if used) and into the internal cavity 38 of the reservoir portion 30. If valve 60 is used, it will permit liquid medicine to flow from the stem portion 14 into the reservoir portion 30, but will prevent the reverse flow of fluid outwardly from the reservoir portion 30 back into the stem portion 14. It should be noted that refilling of the reservoir portion 30 with the same or different liquid medicines may be undertaken at selected time intervals as determined by preliminary pilot studies or changes in clinical symptoms as indicated by, for example, ECoG analysis. Such time intervals will vary, depending on the size and volume characteristics of the treatment apparatus 10 being used, as well the type and severity of the clinical problems to be treated. In any event, refilling in the foregoing manner is accomplished in a rapid, non-invasive manner (e.g. while the reservoir portion 30 is maintained against the round window membrane 155) without the need for additional invasive surgery.

Furthermore, as noted above, the reservoir portion 30 may be initially provided with a supply of a solid (e.g. crystalline), powdered, or gel-type medicine precursor material which may be hydrated/solvated to produce liquid medicine materials in situ after placement of the apparatus 10 in the ear 149 shown in FIG. 9. Fluid (e.g. water or saline solution) addition is typically accomplished in the same manner set forth above using the syringe 170 and needle 172.

Finally, instead of the syringe 170 and needle 172, other commercial fluid delivery systems (not shown) may be used to deliver liquid materials (e.g. water, saline solution, medicines or other hydrating agents) to the reservoir portion 30 of the apparatus 10. An exemplary commercial fluid delivery system suitable for this purpose would involve a product which is known as an osmotic pump. Such a pump is described in Kingma, G. G., et al., "Chronic drug infusion into the scala tympani of the guinea pig cochlea", *Journal of Neuroscience Methods*, 45:127–134 (1992) which is incorporated herein by reference. An exemplary, commercially available osmotic pump may be obtained from the Alza Corp. of Palo Alto, Calif. (USA) and is further generally described in U.S. Pat. Nos. 4,320,758 and 4,976,966. However, it should noted that the present invention shall not be limited to any particular type of delivery system. In fact, other comparable fluid delivery systems may be used in connection with all embodiments of the invention.

Figure 6:
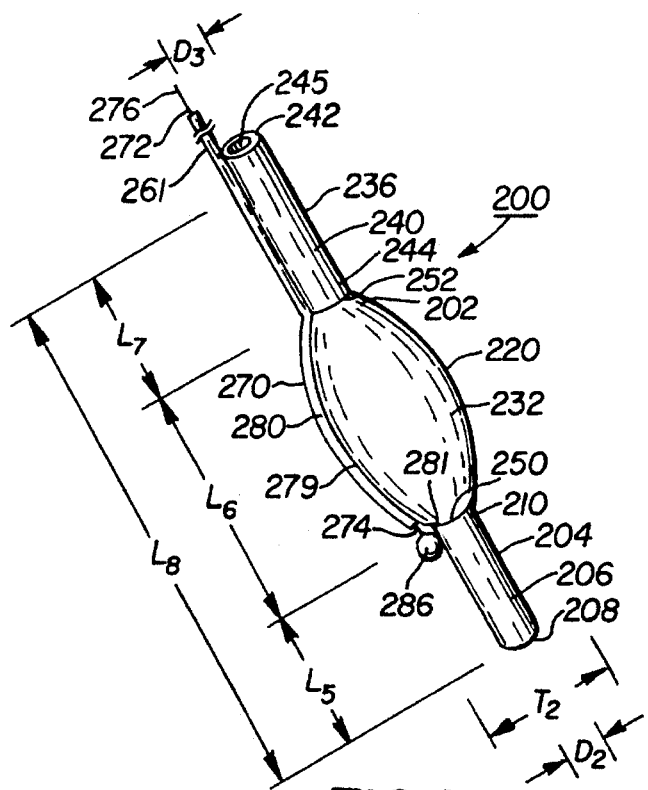
FIG. 6 is an enlarged front perspective view of a multi-functional treatment apparatus for use in the human ear produced in accordance with an alternative embodiment of the present invention.
Figure 7:
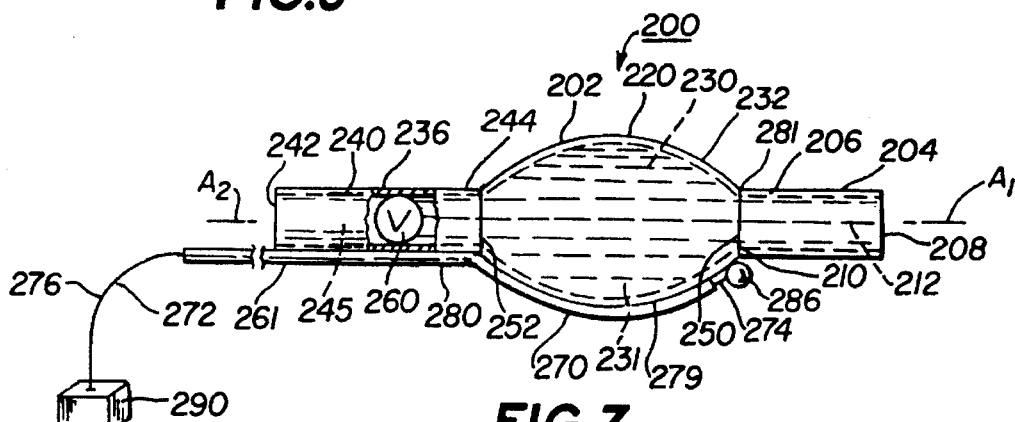
FIG. 7 is an enlarged side view of the alternative treatment apparatus of FIG. 6.
Figure 8:
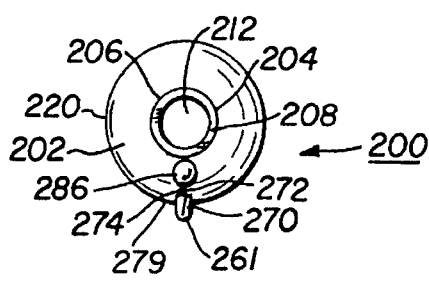
FIG. 8 is an enlarged end view of the alternative treatment apparatus of FIG. 6 showing the first stem portion thereof.

An alternative multi-functional treatment apparatus 200 is illustrated in FIGS. 6–8. Specifically, the apparatus 200 includes a body portion 202 which, as noted above, is preferably of unitary (e.g. single-piece), molded construction. In a preferred embodiment, the body portion 202 is manufactured of a soft, resilient, flexible stretchable), and inert material. The flexibility, elasticity, and softness of the body portion 202 is again of particular importance in order to avoid damage to delicate inner ear tissues during the insertion thereof into a patient. Exemplary construction materials suitable for this purpose are the same as those listed above with respect to the treatment apparatus 10. In addition, in certain instances, it may likewise be desirable to manufacture all or part of the body portion 202 from medical grade silicone rubber (or materials equivalent thereto) impregnated with a radiopaque agent (e.g. $BaSO_4$) which will render all or part of the body portion 202 radiopaque during the application of X-rays.

With continued reference to FIGS. 6–8, the body portion 202 further includes a tubular first stem portion 204. As shown in FIG. 7, the first stem portion 204 includes a continuous side wall 206 which is preferably annular (e.g. ring-like) in cross-section. The first stem portion 204 further includes an open first end 208, a second end 210, and a passageway 212 extending continuously through the first stem portion 204 from the open first end 208 to the second end 210 (FIG. 7). In a preferred embodiment, the first stem portion 204 will have diameter "D2" which is uniform along the entire length thereof from the open first end 208 to the second end 210. Optimally, for use in the human ear, the diameter "$D_2$" of the first stem portion 204 will be about 0.2–2.0 mm. It should again be noted that this diameter range (as well as other quantitative specifications set forth below) is for example purposes only, and the present invention shall not be limited to any particular sizes or dimensions. Furthermore, the length "$L_5$" (FIG. 6) of the first stem portion 204 will preferably be about 0.3–1.5 mm.

With continued reference to FIGS. 6–7, the second end 210 of the first stem portion 204 is operatively and fixedly connected to an enlarged reservoir portion 220 which is designed to retain a supply of liquid medicine therein. As indicated above, it is preferred that the body portion 202 of the treatment apparatus 200 be of unitary (e.g. single-piece) construction. In this regard, the first stem portion 204 and the reservoir portion 220 are, in a preferred embodiment, integrally formed together during production of the apparatus 200. The reservoir portion 220 may involve numerous different external configurations. With reference to FIGS.

6–8, the reservoir portion 220 is configured in an oval (e.g. ovoid) shape. However, the reservoir portion 220 may also resemble a sphere or other comparable configuration. In this regard, the reservoir portion 220 of the apparatus 200 shall not be limited to any particular external shape. As illustrated in FIG. 7, the reservoir portion 220 further includes an internal cavity 230 therein which is adapted to receive liquid medicines, solid (e.g. crystalline) medicines, gel-type medicines or other therapeutic agents as described in greater detail below. An exemplary supply of liquid medicine within the internal cavity 230 is illustrated at reference number 231 in FIG. 7. The internal cavity 230 is surrounded by an external wall 232 as illustrated. While the volumetric capacity of the internal cavity 230 may be suitably varied during manufacture of the medicine delivery apparatus 200, it is preferred that the cavity 230 have a capacity of about 3.0–6.0 ml. Furthermore, as illustrated in FIG. 6, it is preferred that the reservoir portion 220 have a length "$L_6$" of about 3.0–8.8 mm, and a thickness "$T_2$" of about 1.0–8.7 mm.

As illustrated in FIGS. 6–7, the body portion 202 also includes a tubular second stem portion 236 which, in a preferred embodiment is substantially identical in structure to the first stem portion 204. However, as indicated below, it is preferred that the second stem portion 236 be longer than the first stem portion 204. With reference to FIG. 7, the second stem portion 236 includes a continuous side wall 240 which is preferably annular (e.g. ring-like) in cross-section. The second stem portion 236 further includes an open first end 242 (FIGS. 6–7), a second end 244, and a passageway 245 extending continuously through the second stem portion 236 from the first end 242 to the second end 244. In a preferred embodiment, the second stem portion 236 will have a diameter "$D_3$" which is uniform along the entire length thereof from the open first end 242 to the second end 244. Optimally, for use of the apparatus 200 in the human ear, the diameter "$D_3$" will be about 0.2–2.0 mm. Furthermore, the length "$L_7$" (FIG. 6) of the second stem portion 236 will preferably be about 8.8–23.8 mm. The overall length "$L_8$" of the body portion 202 in the present embodiment will preferably be about 12.1–34.1 mm which will readily enable placement of the apparatus 200 within the ear of a patient as described in greater detail below.

The second end 244 of the second stem portion 236 is operatively connected and fixedly secured to (e.g. integrally formed with) the reservoir portion 220 in the same manner set forth above with respect to the first stem portion 204. As shown in FIG. 7, attachment of the second end 210 of the first stem portion 204 and the second end 244 of the second stem portion 236 to the reservoir portion 220 in the foregoing manner enables the passageways 212, 245 in the first and second stem portions 204, 236 to be in fluid communication with the internal cavity 230 of the reservoir portion 220.

So that the medicine delivery apparatus 200 may be readily inserted within the ear of a patient, the first stem portion 204 is positioned on a first side 250 of the reservoir portion 220 and the second stem portion 236 is positioned on a second side 252 of the reservoir portion 220 (FIG. 6). As shown in FIGS. 6–7, the first side 250 and the second side 252 are directly opposite each other. As a result, the first stem portion 204 will preferably be in axial alignment with the second stem portion 236 as illustrated. With reference to FIG. 7, the first stem portion 204 will have a longitudinal axis "$A_1$" which is in alignment with (e.g. collinear with) the longitudinal axis "$A_2$" of the second stem portion 236 so that the first stem portion 204 is positioned at a 180° angle relative to the second stem portion 236.

It should also be noted that the treatment apparatus 200 may optionally include at least one fluid flow control valve 260 therein which is schematically illustrated in FIG. 7. The valve 260 may be positioned within the passageway 212 of the first stem portion 204, within the passageway 245 of the second stem portion 236, or within both of the passageways 212, 245. If positioned within the passageway 212 of the first stem portion 204, the valve 260 will enable one-way fluid flow from the reservoir portion 220 to the first stem portion 204 and outwardly therefrom, while preventing tissue fluids and the like from entering the first stem portion 204 and passing into the reservoir portion 220. If positioned within the passageway 245 of the second stem portion 236, the valve 260 will prevent the reverse flow of liquid medicines outwardly from the reservoir portion 220 into the second stem portion 236. While FIG. 7 illustrates the use of a valve 260 positioned within the passageway 245 of the second stem portion 236, it is to be understood that the present invention shall not be limited exclusively to the use of a single valve 260 as shown, and may likewise encompass the placement of a valve 260 within the passageway 212 of the first stem portion 204. The valve 260 (as used in passageway 212 and/or passageway 245) will be especially useful in embodiments of the present invention which include reservoir portions 220 which contain substantial quantities of liquid medicine therein. The valve 260 may involve numerous commercially-available units including but not limited to the types described above with respect to valve 60. Once again, the present invention shall not be limited in any manner regarding the type of valve 260 which can be used which may also be pressure-sensitive (e.g. capable of allowing fluids therethrough only if they exert a pre-designated fluid pressure on the valve). The valve 260 (if used) may be retained within the passageway 212 and/or passageway 245 by conventional means, including but not limited to those described above with respect to valve 60 (e.g. the use of adhesives or frictional engagement within passageway 212 and/or passageway 245).

Finally, as illustrated in FIG. 7, the treatment apparatus 200 includes electrical potential transmission means 261 fixedly secured to the body portion 202 for receiving electrical potentials from the inner/middle ear and transmitting them out of the ear for the detection and analysis thereof. In a preferred embodiment, the electrical potential transmission means 261 consists of an elongate conductive member 270 fixedly secured to the body portion 202 as illustrated. The elongate conductive member 270 is substantially identical to the conductive member 70 described above, and may involve a variety of different structures. For example, it is preferred that the elongate conductive member consist of a thin wire 272 manufactured from the same materials used to construct wire 72. The wire 272 (e.g. of the same general type and gauge as wire 72) includes a proximal end 274 and a distal end 276 illustrated in FIG. 6. The wire 272 is fixedly secured to the body portion 202 of the apparatus 200 in any desired or suitable position thereon. In the embodiment of FIGS. 6–7, the elongate conductive member 270 (e.g. wire 272) is secured to the body portion 202 of the apparatus 200 along the lower surface 279 thereof. Attachment may be accomplished using an adhesive of the type set forth above relative to attachment of the conductive member 70 to the treatment apparatus 10 (e.g. a conventional cyanoacrylate or epoxy resin adhesive). Furthermore, the wire 272 is preferably coated with a layer 280 of an insulating material. Exemplary insulating materials include but are not limited to heat shrinkable Teflon® coating materials known in the art.

Also, as described above with respect to the conductive member 70, it should be noted that the conductive member 270 may involve other structures equivalent to the wire 272 including but not limited to the use of a relatively flat, flexible metallic strip (not shown).

With continued reference to FIGS. 6–7, the proximal end 274 of the wire 272 is preferably positioned adjacent the second end 210 of the first stem portion 204 (e.g. at the juncture 281 between the first stem portion 204 and the reservoir portion 220 as shown in FIG. 6). Alternatively, the proximal end 274 of the wire 272 may be positioned adjacent the open first end 208 of the first stem portion 204, although the previously described orientation is preferred. Likewise, in a preferred embodiment, the proximal end 274 of the wire 272 includes a conductive spherical member 286 secured thereto (e.g. integrally formed thereon) optimally manufactured of the same material used to construct the wire 272. Use of the spherical member 286 facilitates direct contact between the wire 272 and ear tissues of concern so that electrical potentials (ECoG potentials) may be received therefrom. It should likewise be noted that while the conductive member 270 (e.g. wire 272) is discussed herein with reference to the receipt of electrical potentials, it may also be possible to use the conductive member 270 to apply electrical potentials to tissues of interest in order to measure responsive stimuli therefrom. Thus, the conductive member 270 (e.g. wire 272) of the present invention shall not be exclusively limited to the receipt of electrical potentials.

Figure 10:
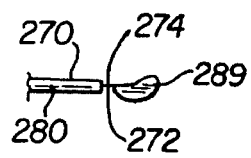
FIG. 10 is an enlarged side view of the proximal end of an alternative embodiment of the conductive wire used in connection with the treatment apparatus of FIG. 6 to receive/transmit electrical signals.

In an alternative embodiment as illustrated in FIG. 10, the proximal end 274 of the wire 272 may include a rounded club or hook-like portion 289 instead of the spherical member 286. Thus, the proximal end 274 of the wire 272 may encompass a variety of different forms, and shall not be limited to any single structure or design. In addition, as illustrated in FIG. 6, the distal end 276 of the wire 272 preferably extends beyond the open first end 242 of the second stem portion 236 as illustrated. Upon insertion of the apparatus 200 into the ear of a patient, the distal end 276 of the wire 272 will preferably pass through the incised tympanic membrane, along the external auditory canal of the patient, and will preferably terminate at a position outside of the patient's ear. When oriented in this manner, the distal end 276 is readily connected to an external monitoring apparatus 290 (FIG. 7) of conventional design which may be used to analyze and quantify electrical potentials from the inner ear. In a preferred embodiment, the monitoring apparatus 290 is of the same type as monitoring apparatus 90. Furthermore, as previously described with respect to the conductive member 70, the conductive member 270 is designed to receive resting or evoked electrical potentials from inner ear tissues in accordance with known ECoG procedures. Thus, all of the information, techniques, and materials set forth above regarding use of the conductive member 70 for ECoG purposes is equally applicable to the conductive member 270. In a preferred and optimum embodiment, the total length of the wire 272 from the proximal end 274 to the distal end 276 (measured when straight) will be about 5.0 cm.

The treatment apparatus 200 of the present invention is used in a somewhat different manner compared with the apparatus 10. Specifically, the apparatus 200 is surgically inserted within the ear of a patient so that the first stem portion 204 (e.g. at least the open first end 208 thereof) is positioned within the inner ear. Specifically, the open first end 208 of the first stem portion 204 will be positioned against and in direct contact with the inner ear tissues/tissue regions to be treated so that liquid medicines from the internal cavity 230 of the reservoir portion 220 may be drawn outwardly therefrom and through the first stem portion 204 by capillary action (described in greater detail below). It is likewise preferred that the reservoir portion 220 be positioned entirely within the middle ear as described below. Furthermore, at least a section of the second stem portion 236 (including the open first end 242 thereof) is preferably positioned so that it will extend through the incised tympanic membrane and into the external auditory canal of the patient at a location remotely spaced from the middle ear. In this manner, the reservoir portion 220 may be readily supplied with liquid medicines or other fluid materials as needed through the external auditory canal and; second stem portion 236 without additional surgical intervention in most instances. In addition, the treatment apparatus 200 is manipulated during or after insertion so that the proximal end 274 (e.g. spherical member 286) of the elongate conductive member 270 (e.g. wire 272) is in direct physical contact with the ear tissues of concern so that electrical potentials may be received therefrom as described in further detail below.

Figure 11:
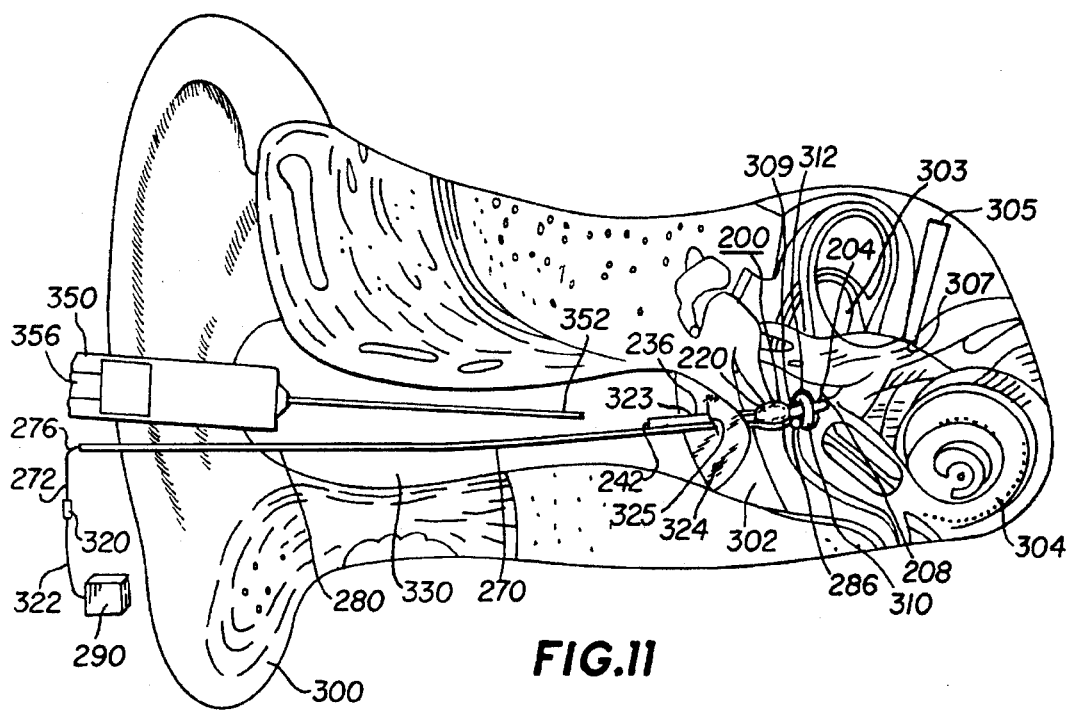
FIG. 11 is a schematic, partial cross-sectional view of the ear of a human subject illustrating the treatment apparatus of FIG. 6 inserted therein.

FIG. 11 is a schematic, partial cross-sectional view of the ear 300 of a human subject illustrating the apparatus 200 of FIG. 6 inserted therein. As shown, the apparatus 200 is positioned so that the reservoir portion 220 is entirely within the middle ear (generally designated in FIG. 11 at reference number 302). The first stem portion 204 (and the open first end 208 thereof) is positioned within the inner ear (generally designated in FIG. 11 at reference number 303) which includes the cochlea 304, the endolymphatic sac 305, and the endolymphatic duct 307. As described below, the first stem portion 204 is positioned within an opening 309 formed through the stapes footplate 310 and oval window 312 thereunder. As a result, the first end 208 of the first stem portion 204 may come in direct physical contact with the inner ear tissues, fluids, and/or tissue regions of concern so that liquid medicine materials from the reservoir portion 220 may be delivered thereto by capillary action through the passageway 212 of the first stem portion 204 and out of the open first end 208 thereof.

With continued reference to FIG. 11, the spherical member 286 associated with the proximal end 274 of the conductive member 270 is positioned adjacent to and in direct contact with the stapes footplate 310 in the middle ear (and other tissues associated therewith) so that electrical potentials originating within the inner ear 303 may be received therefrom. In an alternative embodiment, if the proximal end 274 and spherical member 286 are positioned adjacent the open first end 208 of the first stem portion 204, then these components will come in direct contact with inner ear tissues of concern. As indicated above, such potentials may be generated using externally generated tone bursts, clicks, pips and the like in accordance with standard ECoG procedures. The distal end 276 of the wire 272 associated with the conductive member 270 (which may have a portion of the layer 280 of insulating material removed therefrom outside of the ear 300) is positioned outwardly from the ear 300 as illustrated. The distal end 276 is thereafter connected using a standard miniature connecting clip 320 to monitoring apparatus 290 via conductive conduit 322. The monitoring apparatus 290 is used to analyze and quantify electrical potentials ultimately received from the inner ear 303.

Finally, as shown in FIG. 11 and indicated above, a substantial section 323 of the second stem portion 236 (including the open first end 242 thereof) passes through an incision 325 in the tympanic membrane 324 and resides within the external auditory canal 330 of the ear 300. Alternatively, the section 323 of the second stem portion 236 may pass beneath a tympanomeatal flap (not shown) depending on the techniques chosen by the surgeon. In order to supply the internal cavity 230 of the reservoir portion 220 with liquid medicines (e.g. immediately after insertion of the treatment apparatus 200, when initial supplies of liquid medicine within the reservoir portion 220 have been depleted, or when a change in the type of delivered medicine is desired), a conventional syringe 350 having a hollow needle 352 attached thereto is used in the same manner described above with respect to treatment apparatus 10 and syringe 170. Specifically, the syringe 350 is initially filled with a selected liquid medicine. The needle 352 is thereafter inserted into the external auditory canal 330 and through the open first end 242 of the second stem portion 236. Next, pressure is exerted on the plunger 356 of the syringe 350 in order to deliver the liquid medicine from the syringe 350 through the needle 352 and into the second stem portion 236. The liquid medicine thereafter flows from the second stem portion 236 through the valve 260 (if used) and into the reservoir portion 220. If valve 260 is used, it will permit liquid medicine to flow from the second stem portion 236 into the reservoir portion 220, but will prevent the reverse flow of fluid outwardly from the reservoir portion 220 back into the second stem portion 236. It should again be noted that refilling of the reservoir portion may be undertaken at selected time intervals as determined by preliminary pilot studies or changes in clinical symptoms as indicated by, for example, ECoG analysis. In any event, refilling in the foregoing manner is accomplished in a rapid, non-invasive manner without the need for additional surgery.

In addition, as noted above, the reservoir portion 220 may be initially provided with a supply of a solid (e.g. crystalline), powdered, or gel-type medicine material which may be hydrated/solvated to produce liquid medicines in situ after placement of the apparatus 200 in the ear 300 shown in FIG. 11. The addition of a selected fluid (e.g. water, saline solution, or the like) is typically accomplished in the same manner set forth above using the syringe 350 and needle 352. Specifically, an additional supply of therapeutic agents or liquid medicine materials may be delivered through the external auditory canal 330 into the first end 242 of the second stem portion 236 of the apparatus 200 using the syringe 350 and the needle 352. In a preferred embodiment, this activity takes place while the reservoir portion 230 is maintained within the middle ear 302 and the first end 208 of the first stem portion. 204 is maintained within the inner ear 303. It should also be noted that alternative fluid delivery devices may be used in connection with the apparatus 200 other than syringe 350 including but not limited to the osmotic pump systems described above relative to apparatus 10.

With respect to surgical insertion of the treatment apparatus 200, a number of different approaches may be used, and the present invention shall not be limited to any specific surgical technique. However, an exemplary technique for inserting the apparatus 200 so that it is positioned as illustrated in FIG. 11 would first involve exploration of the middle ear 302 via a tympanomeatal flap exposing the middle ear cleft and the ossicular chain. The stapes footplate 310 (and underlying oval window 312) is then fenestrated to form opening 309 therethrough using a conventional microdrill unit or standard medical laser system (e.g. involving a commercially-available $CO_2$ laser, an argon laser, or a tunable dye laser). The opening 309 as described above functions as an access port in the ear between the middle ear 302 and the inner ear 303. The apparatus 200 is then positioned within the middle ear 302, and the first stem portion 204 placed through the opening 309 in the stapes footplate 310 and oval window 312. Alternatively, the first stem portion 204 may be placed through a similar opening (access port) formed in the same manner through the bony cochlear or vestibular labyrinth. Thus, the present invention shall not be limited to any particular location with respect to the opening 309 which may be placed in any suitable position so that access can be made from the middle ear 302 to the inner ear 303.

As noted above, all or part of the apparatus 200 may be made radiopaque by impregnation thereof with a marker composition (e.g. $BaSO_4$ or other comparable material) during production of the apparatus 200. In a preferred and optimum embodiment, only the first stem portion 204 will be impregnated with the marker composition so that the first stem portion 204 within the inner ear 303 may be readily identified and distinguished from the remainder of the apparatus 200. Upon insertion of the first stem portion 204 of the apparatus 200 into the inner ear 303, the first stem portion 204 may come in contact with a variety of inner ear tissue/fluid materials including but not limited to the perilymph (an inner ear fluid which is low in potassium ions and high in sodium ions), the saccular membrane, the endolymph (an inner ear fluid which is low in sodium ions and high in potassium ions), and the internal structures of the cochlea or vestibular labyrinth. The apparatus 200 may then be used to deliver needed liquid medicine materials to these structures in a highly efficient and sustained manner. As noted above, it is preferred that any fluid materials within the apparatus 200 be present in a sufficient quantity so that they will entirely fill at least the reservoir portion 220 and the first stem portion 204. As a result, such fluid materials will be present at the open first end 208 of the first stem portion 204. When the first end 208 of the first stem portion 204 is placed in direct contact with the selected inner ear tissues by surgical manipulation of the apparatus 200, 1fluid materials will be drawn therefrom by capillary action.

Figure 12:
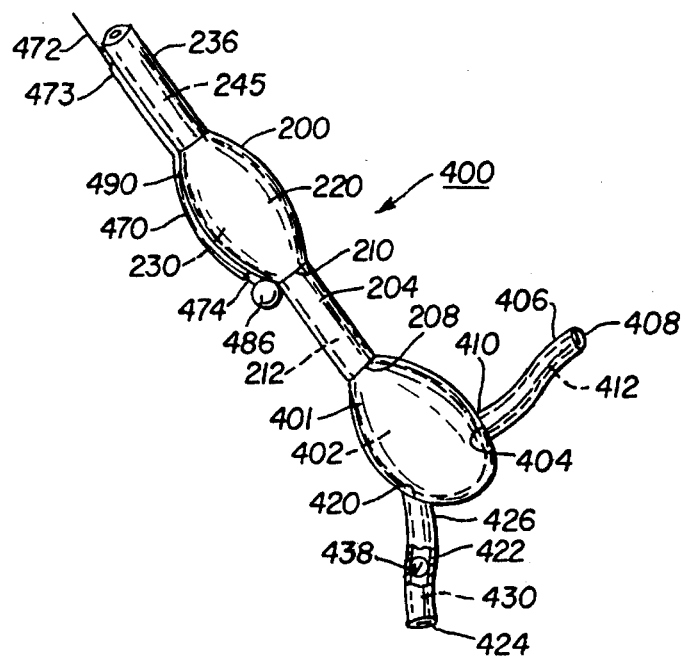
FIG. 12 is an enlarged front perspective view of a further alternative multi-functional treatment apparatus wherein the apparatus of FIG. 6 has been modified to include additional structural components.

Finally, it should be noted that the treatment apparatus 200 may be selectively modified to include various additional components which shall be encompassed within the scope of this invention. For example, as illustrated in FIG. 12, the apparatus 200 is modified to include an additional grouping of components thereon to produce an alternative treatment apparatus 400. All of the information, techniques, and characteristics set forth above regarding the apparatus 200 are equally applicable to the apparatus 400 except as otherwise indicated below.

In the embodiment of FIG. 12, the apparatus 400 includes an additional reservoir portion and at least one additional tubular stem portion. For example, operatively connected to and fixedly secured to the first end 208 of the first stem portion 204 is a second reservoir portion 401 which is comparable in function, structure, and construction to the reservoir portion 220 (which, in this embodiment, shall be deemed the first reservoir portion 220). The second reservoir portion 401 includes an internal cavity 402 therein which is substantially identical in configuration and capacity to cavity 230 in the first reservoir portion 220. In accordance with this embodiment, the passageway 212 in the first stem portion 204 is in fluid communication with the internal cavity 402 as shown. It should be noted that, in this embodiment, the first and second reservoir portions 220, 401 may each have optional fluid transfer means therein (not shown) of the same general type described above with respect to fluid transfer means 43 in apparatus 10.

Extending outwardly from the second reservoir portion 401 at position 404 thereon is an additional tubular stem portion (hereinafter designated as third stem portion 406) having an open first end 408, a second end 410, and a passageway 412 extending continuously through the third stem portion 406 from the open first end 408 to the second end 410. The passageway 412 is in fluid communication with the internal cavity 402 of the second reservoir portion 401. In a preferred embodiment, the third stem portion 406 is substantially identical in structure, function, and size to the first stem portion 204 as described above.

Extending outwardly from the second reservoir portion 401 at position 420 thereon is an even further additional tubular stem portion (e.g. hereinafter designated as fourth stem portion 422) having an open first end 424, a second end 426, and a passageway 430 extending continuously through the fourth stem portion 422 from the open first end 424 to the second end 426 thereof. The passageway 430 is in fluid communication with the internal cavity 402 of the second reservoir portion 401. Otherwise, the fourth stem portion 422 is substantially identical in structure, function, and size to the first stem portion 204 as described above. One or more of the third and fourth stem portions 406, 422 may include at least one valve 438 therein as shown in FIG. 12 which illustrates a single valve 438 positioned within the fourth stem portion 422. The valve 438 is preferably of the same type and configuration as the valves 60, 260 described above, and is mounted/positioned within third and/or fourth stem portions 406, 422 in the same manner described herein relative to valves 60, 260. One or more of the third and fourth stem portions 406, 422 may be made radiopaque during production of the alternative treatment apparatus 400 by the incorporation of a marker composition therein (e.g. BaSO$_4$ or other comparable material). In addition, at least one valve (not shown) of the same type as valve 438 may be positioned within the internal cavity 402 of the second reservoir portion 401 to control the flow of liquid materials into and out of the second reservoir portion 401. Finally, the apparatus 400 may further include a conductive member 470 of the same type set forth above regarding the conductive member 70 in apparatus 10, with all of the features and functional capabilities of conductive member 70 being applicable to conductive member 470. As illustrated in FIG. 12, the conductive member 470 will preferably consist of an elongate wire 472 surrounded by a layer 473 of insulating material of the same type as layer 73 in the first embodiment of the present invention. The wire 472 likewise has the same characteristics as wire 72, with the proximal end 474 of the wire 472 having a spherical member 486 thereon as illustrated. The conductive member 470 (e.g. wire 472) is preferably secured to the underside 490 of the apparatus 400 shown in FIG. 12 adjacent the second stem portion 236 and the first reservoir portion 220. Affixation may be accomplished using the same materials set forth above regarding the conductive member 70. The spherical member 486 is preferably positioned adjacent the second end 210 of the first stem portion 204 as illustrated. However, it should be noted that the position of the conductive member 470 may be suitably varied and located at any position on the apparatus 400. Also, the conductive member 470 may be extended (lengthened) so that one or more spherical members (not shown) of the same type as spherical member 486 are located at various positions on the apparatus 400 (e.g. adjacent the third and/or fourth stem portions 406, 422). The apparatus 400 shall not be limited with respect to the length of the conductive member 470 (e.g. wire 472) or the number and placement of the spherical members 486 operatively connected to the conductive member 470. The conductive member 470 and components associated therewith are designed for ECoG monitoring purposes as described herein.

It should be noted that, with respect to all of the embodiments described herein involving apparatus 10, apparatus 200, and apparatus 400, such devices shall not be limited regarding the number and orientation of reservoir portions, valves, and/or stem portions which are used therewith. Also, as indicated above with respect to apparatus 200, the first stem portion 204 in apparatus 400 will preferably be in axial alignment with the second stem portion 236 as illustrated. In this configuration, first stem portion 204 is located on first side 250 of the first reservoir portion 220, and the second stem portion 236 is located on second side 252 of the first reservoir portion 220 (FIG. 7). As previously discussed, first side 250 is directly opposite the second side 252 so that the first stem portion 204 is positioned at a 180° angle relative to the second stem portion 236.

The alternative treatment apparatus 400 illustrated in FIG. 12 provides all of the benefits set forth above regarding treatment apparatus 200, but is further characterized by an improved medicine-retaining capacity (due to the use of dual reservoir portions 220, 401). Also, the use of additional stem portions (e.g. third and fourth stem portions 406, 422) enables a greater distribution of liquid medicine materials to a variety of inner ear structures and related regions. In a preferred embodiment, the use of third and fourth stem portions 406, 422 enables liquid medicines to be delivered by capillary action to the endolymphatic sac/endolymphatic duct, as well as to the subarachnoid space adjacent the inner ear. Surgical insertion of the alternative medicine treatment apparatus 400 may be accomplished in a number of different ways. For example, the apparatus 400 may be implanted into the endolymphatic sac and duct using standard techniques and procedures as described in Pillsbury, H. C., III et al. (ed.), *Operative challenges in Otolaryngology—Head and Neck Surgery*, Yearbook Medical Procedures, Chicago, 93–111: (1990)—(article therein presented in Chapt. 7 entitled "Nondestructive Surgery for Vertigo—Approach of I. Kaufman Arenberg, et al.) which is incorporated herein by reference. Specifically, the first end 424 of the fourth stem portion 422 is placed through the endolymphatic sac into the subarachnoid space (using a procedure described in House, W. F., "Subarachnoid shunt for drainage of hydrops: a report of 146 cases", *Laryngoscope*, 75:1547–1553 (1965) incorporated herein by reference). The second reservoir portion 401 remains at the endolymphatic sac. The rest of the apparatus 400 is then brought into the middle/inner ear via a posterior tympanotomy from the mastoid cavity in the same manner traditionally used in connection with cochlear implants as described in Pillsbury, H. C., III et al. (ed.), *Operative challenges in Otolaryngology—Head and Neck Surgery*, Yearbook Medical Procedures, Chicago, 139–145: (1990)—(article therein presented in Chapt. 10 entitled "Cochlear Implants—Approach of William M. Luxford, et al.) which is also incorporated herein by reference. In this regard, the first reservoir portion 220 is positioned at the round window membrane in the middle ear, with the second stem portion 236 and distal portions of the elongate conductive member 470 being brought through the tympanic membrane and external auditory canal in the same manner set forth above regarding apparatus 200. It should be noted that surgical insertion of the apparatus 400 may be undertaken in a number of different ways, and the present invention shall not be limited to the specific procedure outlined above.

Finally, the second reservoir portion 401, third stem portion 406 and fourth stem portion 422 are each preferably manufactured from the same materials used to produce the remaining portions of the apparatus 400 which is optimally of unitary construction.

In a still further alternative embodiment of the present invention, means are provided wherein changes in inner ear fluid pressure, temperature, and/or volume levels may be accomplished. As previously indicated, a precise balance exists with respect to the fluids of the inner ear (e.g. the endolymph and the perilymph). These fluids are maintained within discrete tissue structures, with the endolymph being retained within the endolymphatic system and the perilymph being held within the perilymphatic system. If a precise balance does not exist with respect to these fluid materials, numerous problems may result as previously described regarding endolymphatic hydrops, endolymphatic hypertension, and/or perilymphatic hypertension. In the present invention, means are provided wherein pressure changes relative to the foregoing fluids may be accomplished in a substantially non-invasive manner. As described below, these changes are undertaken by the direct application of physical pressure to selected tissue structures, with such physical pressure being transmitted directly to the foregoing fluids. Alternatively, such changes in fluid pressure may be accomplished by increasing or decreasing the temperature of the fluids which cause corresponding changes in fluid volume and pressure levels. For example, an increase in fluid temperature will result in a thermal expansion of the fluid, thereby increasing its volume and pressure levels in accordance with known physical relationships involving fluid pressure, temperature, and volume.

Figure 13:
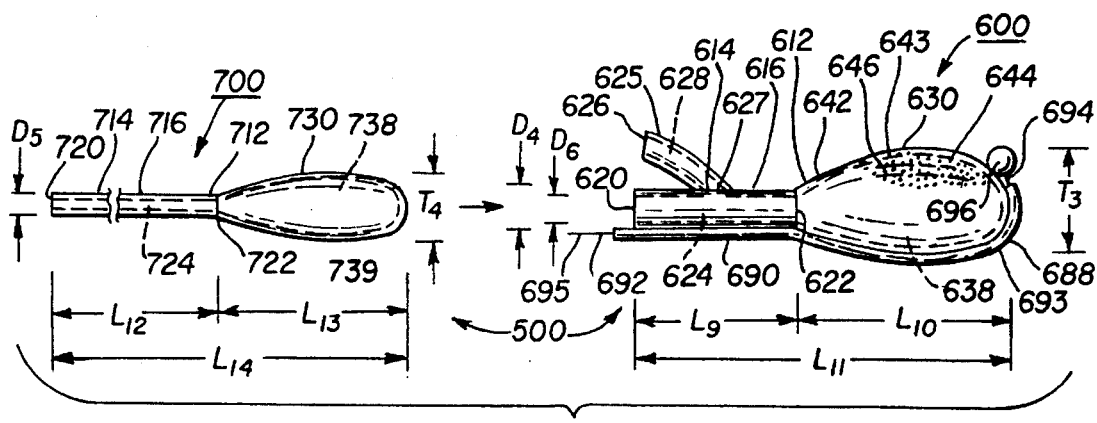
FIG. 13 is an enlarged, exploded side view of a specialized multi-component treatment system designed to induce temperature, volume, and pressure changes with respect to the fluids of the human ear and deliver medicine materials to internal ear tissues.

To specifically achieve the foregoing changes in fluid temperature, pressure and volume levels, a modified treatment system 500 illustrated in FIG. 13 is provided. Basically, the system 500 includes two main components. The first component involves a primary treatment apparatus 600 which is illustrated in FIG. 13. From an external perspective, apparatus 600 is substantially identical to apparatus 10 illustrated in FIG. 1, with all of the information described above involving apparatus 10 being applicable to apparatus 600 unless otherwise indicated. As shown in FIG. 13, the apparatus 600 includes a body portion 612 which, as noted above, is preferably of unitary (e.g. single-piece), molded construction. In a preferred embodiment, the body portion 612 is manufactured of a soft, resilient, elastic, and biologically inert material with a preferred thickness of about 0.03–0.07 mm in order to facilitate stretching of the apparatus 600 as described below. Exemplary construction materials suitable for this purpose include but are not limited to medical grade silicone rubber and other equivalent compositions.

In addition, in certain instances, it may likewise be desirable to manufacture all of part of the body portion 612 from medical grade silicone rubber impregnated with $BaSO_4$ or any other suitable materials having similar characteristics which will render the body portion 612 radiopaque when X-rays are applied thereto. This will enable the treating physician to accurately determine the precise location of the apparatus 600 within a patient after insertion.

With continued reference to FIG. 13, the body portion 612 further includes a tubular primary stem portion 614. As shown in FIG. 13, the primary stem portion 614 includes a continuous side wall 616 which is preferably annular circular/ring-like) in cross-section. The primary stem portion 614 further includes an open first end 620, a second end 622, and a passageway 624 extending continuously through the primary stem portion 614 from the open first end 620 to the second end 622. In a preferred embodiment for use in connection with the human ear, the primary stem portion 614 will have a diameter "$D_4$" and length "$L_9$" comparable to the diameter "$D_1$" and length "$L_1$" of the stem portion 14 in the apparatus 10 of FIG. 1.

Extending outwardly from the primary stem portion 614 as illustrated in FIG. 13 is a secondary stem portion 625 having an open first end 626, and a second end 627 which is operatively connected to the primary stem portion 614 between the first end 620 and the second end 622. The secondary stem portion 625 has an internal passageway 628 which extends continuously from the first end 626 to the second end 627 and is in fluid communication with the passageway 624 through the primary stem portion 614. The function of the secondary stem portion 625 will be described below.

With continued reference to FIG. 13, the second end 622 of the primary stem portion 614 is operatively and fixedly connected to an enlarged reservoir portion 630 which is designed to retain a supply of liquid, gel-type, or solid (e.g. crystalline or powdered) medicines therein. As indicated above, it is preferred that the body portion 612 of the primary treatment apparatus 600 be of unitary (e.g. single-piece) molded construction. In this regard, the primary stem portion 614 and the reservoir portion 630 are, in a preferred embodiment, integrally formed together during production of the apparatus 600.

The reservoir portion 630 may involve numerous different external configurations such as those described above relative to reservoir portion 30. Furthermore, as illustrated in FIG. 13, the reservoir portion 630 includes an internal cavity 638 which is adapted to receive liquid, gel-type, or solid medicines therein as described in greater detail below. Attachment of the primary stem portion 614 to the reservoir portion 630 in the foregoing manner enables the passageway 624 in the primary stem portion 614 to be in fluid communication with the internal cavity 638 in the reservoir portion 630. While the volumetric capacity of the internal cavity 638 may be suitably varied during manufacture of the apparatus 600, it is preferred that the internal cavity 638 have a capacity of about 3.0–6.0 ml. Furthermore, as illustrated in FIG. 13, it is preferred that the reservoir portion 630 have a length "$L_{10}$" and thickness "$T_3$" approximately equal to the length "$L_2$" and thickness "$T_1$" of the reservoir portion 30 in the apparatus 10 described above. Likewise, the overall length "$L_{11}$" of the body portion 612 will preferably be about equal to the length "$L_3$" of the body portion 12 indicated above.

The internal cavity 638 of the reservoir portion 630 is surrounded by an exterior wall 642. So that medicine materials retained within the internal cavity 638 of the reservoirs portion 630 may be effectively delivered to desired tissues within the middle/inner ear, the wall 642 includes fluid transfer means therein generally designated at reference number 643 in FIG. 13. The fluid transfer means 643 may consist of a fenestrated zone 644 in the wall 642 of the reservoir portion 630 as illustrated. The term "fenestrated" as used herein involves a portion of the wall 642 having a plurality of pores 646 (enlarged for the sake of clarity in FIG. 13) therethrough. The pores 646 function in the same manner as the pores 46 in the apparatus 10 described above. Likewise, all of the other characteristics of the pores 646 are substantially identical to tile characteristics of pores 46 (e.g. size, quantity, etc.). As far as the fluid transfer means 643 is concerned, other systems may be used instead of the pores 646 for allowing liquid medicines to pass out of the internal cavity 638 of the reservoir portion 630 during use of the apparatus 600. For example, the fluid transfer means 643 may consist of a semi-permeable membrane (not shown) of the type described above relative to membrane 54 or a micropore filter of conventional design as indicated above relative to apparatus 10.

Finally, as illustrated in FIG. 13, the apparatus 600 includes electrical potential transmission means 688 fixedly secured to the body portion 612 for receiving electrical potentials from middle/inner ear tissues and transmitting them out of the ear for the detection and analysis thereof. In a preferred embodiment, the electrical potential transmission means 688 will consist of an elongate conductive member 690 (e.g. in the form of a wire 692) of exactly the same type as the conductive member 70 and wire 72. As shown in FIG. 13, the wire 692 is covered with a layer 693 of insulating material of the same type used in connection with the layer 73 of insulation indicated above. Likewise, the conductive member 690 (e.g. the wire 692) has a proximal end 694 and a distal end 695. Accordingly, all of the information set forth above relative to the structure, position, and function of the conductive member 70 is equally applicable to the conductive member 690 which likewise preferably includes a conductive spherical member 696 secured thereto (e.g. integrally formed as a part of the wire 692). The spherical member 696 is substantially identical to the spherical member 86 used in connection with the wire 72. As a result, ECoG analyses may be undertaken in a rapid and efficient manner.

So that the system 500 is capable of modifying the pressure, temperature, and volumetric characteristics of inner ear fluid materials (e.g. endolymph and/or perilymph), the system 500 further includes a second component which is designed for insertion within the primary treatment apparatus 600. With continued reference to FIG. 13, the body portion 612 of the apparatus 600 is sized to receive an inflatable insert member 700 having a body portion 712 which is preferably of unitary (e.g. single-piece), molded construction. In a preferred embodiment, the body portion 712 is manufactured of a soft, resilient, stretchable, and biologically inert material. The stretchability of the body portion 712 is especially important for the reasons described below. Exemplary construction materials suitable for this purpose include but are not limited to medical grade silicone or other equivalent materials having a preferred thickness of about 0.03–0.07 mm.

In addition, in certain instances, it may again be desirable to manufacture all of part of the body portion 712 from medical grade silicone rubber impregnated with $BaSO_4$ or any other suitable materials having similar characteristics which will render the body portion 712 radiopaque when X-rays are applied thereto. This will enable the treating physician to accurately determine the precise location of the apparatus 600 and insert member 700 within a patient.

As shown in FIG. 13, the body portion 712 further includes an elongate tubular portion 714. The tubular portion 714 includes a continuous side wall 716 which is preferably annular (e.g. circular or ring-like) in cross-section. The tubular portion 714 further includes an open first end 720, a second end 722, and a passageway 724 extending continuously through the tubular portion 714 from the first end 720 to the second end 722. In a preferred embodiment for use in connection with the human ear, the tubular portion 714 will have a diameter "$D_5$" which is uniform along the entire length thereof from the first end 720 to the second end 722. This diameter "$D_5$" will optimally be smaller than the diameter "$D_6$" of the passageway 624 in the primary stem portion 614 of the apparatus 600 so that the tubular portion 714 of the insert member 700 may be readily placed within the primary stem portion 614 of the apparatus 600. Also, the foregoing relationship between "$D_5$" and "$D_6$" ensures that fluid materials may be readily delivered from external sources into the reservoir portion 630 of the apparatus 600 via the primary stem portion 614. In a preferred embodiment for use in connection with the human ear, the unexpanded diameter "$D_5$" of the tubular portion 714 will be about 0.2–0.6 mm, and the diameter "$D_6$" of the passageway 624 in the apparatus 600 will be about 0.5–0.8 mm. Furthermore, the length "$L_{12}$" (FIG. 13) of the tubular portion 714 will preferably be longer than the length "$L_9$" of the primary stem portion 614 of the apparatus 600. Optimally, "$L_{12}$" will be about 10.0–30.0 mm.

With continued reference to FIG. 13, the second end 722 of the tubular portion 714 is operatively and fixedly connected to a bulb-like fluid receiving portion 730. As indicated above, it is preferred that the body portion 712 of the insert member 700 be of unitary (e.g. single-piece) molded construction. In this regard, the tubular portion 714 and the fluid receiving portion 730 are, in a preferred embodiment, integrally formed together during production.

Figure 14:
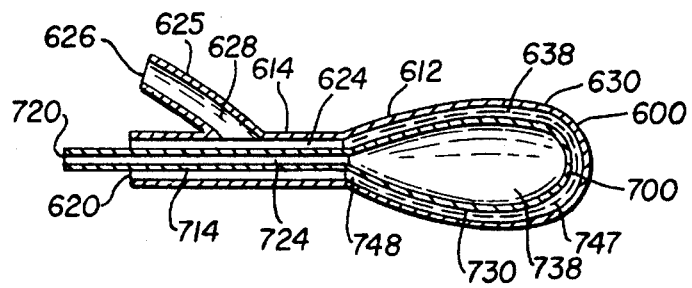
FIG. 14 is an enlarged, assembled, cross-sectional side view of the multi-component treatment system of FIG. 13.

The fluid receiving portion 730 may involve numerous different external configurations. With reference to FIG. 13, the fluid receiving portion 730 is configured in an oval (e.g. ovoid) shape substantially identical in configuration with the configuration of the internal cavity 638 in the apparatus 600 as illustrated. While the present invention shall not be limited with respect to the shape of the fluid receiving portion 730, it is preferred that the fluid receiving portion 730 have a shape which does, in fact, correspond with the shape of the internal cavity 638 in the apparatus 600. The fluid receiving portion 730 further includes an internal cavity 738 surrounded by an exterior wall 739. The cavity 738 is adapted to receive a supply of pressurized liquid or gas therein. For the purposes of this invention, the term "fluid" shall be used to signify either liquids or gases supplied to the internal cavity 738 of the fluid receiving portion 730. In addition, as shown in FIG. 13, attachment of the tubular portion 714 to the fluid receiving portion 730 in the foregoing manner enables the passageway 724 in the tubular portion 714 to be in fluid communication with the internal cavity 738 in the fluid receiving portion 730. While the volumetric capacity of the internal cavity 738 may be;suitably varied during manufacture of the insert member 700, it is preferred that the internal cavity 738 have an ambient, unexpanded capacity of about 0.50–1.0 ml. However, in view of the stretchable nature of the fluid receiving portion 730 as described above, this numerical range may increase substantially, depending on the amount of fluid materials being delivered thereto as well as the pressure of such materials. Furthermore, as illustrated in FIG. 13, it is preferred that the fluid receiving portion 730 have a length "$L_{13}$" of about 2.0–8.0 mm and a thickness "$T_4$" of about 0.5–7.0 mm which are less than the length "$L_{10}$" and thickness "$T_3$" of the reservoir portion 630 of the apparatus 600. In fact, the dimensions of the fluid receiving portion 730 are smaller than those of the internal cavity 638 of the reservoir portion 630 in order to enable the portion 730 to readily fit within the internal cavity 638 as shown in FIG. 14 (which involves an enlarged cross-sectional view of the apparatus 600 having the insert member 700 mounted therein.) As a result, fluid materials 747 (FIG. 14) will be able to reside within the internal cavity 638. Likewise, as noted above, the tubular portion 714 is smaller than the passageway 624 in the primary stem portion 614 so that the foregoing fluid materials may be supplied to the internal cavity 638 of the primary treatment apparatus 600 via passageways 624, 628 (FIGS. 14). In addition, it is important to note that the total length "$L_{14}$" of the insert member 700 as shown in FIG. 13 is about 13.0–38.0 mm.

It should also be noted that the insert member 700 may be positioned within the body portion 612 of the apparatus 600 in a number of different ways. For example, during the manufacturing process, the body portion 612 of the apparatus 600 may be molded directly over and around the previously formed insert member 700. Alternatively, in view of the highly stretchable nature of the apparatus 600, the insert member 700 may be suitably urged into the apparatus 600 using any blunt, elongate instrument. As the insert member 700 is being urged into the apparatus 600, the body portion 612 will stretch, thereby facilitating placement of the insert member 700 in position within the body portion 612.

As noted above, FIG. 14 involves a cross-sectional view of the system 500 wherein the insert member 700 is positioned within the apparatus 600. In FIG. 14, the elongate conductive member 690 has been omitted for the sake of clarity. Because the insert member 700 in a non-inflated state has smaller overall dimensions than the interior regions of the apparatus 600 (e.g. the tubular portion 714 is smaller than the passageway 624 and the fluid receiving portion 730 is smaller than the internal cavity 638), an open zone 748 will exist around the insert member 700 as shown. The function of this zone 748 will be described below.

The apparatus 600 (with the insert member 700 therein) is then surgically inserted within a patient so that the reservoir portion 630 is located in the middle ear and in direct physical contact with a selected middle-inner ear interface tissue structure (e.g. the round window membrane). Likewise, the apparatus 600 is inserted so that at least part of the primary stem portion 614 (e.g. the open first end 620 thereof) is positioned within the external auditory canal at a position remotely spaced from the middle ear (see FIG. 15 described below). Surgical insertion and placement in this manner is again normally accomplished via an incision in the tympanic membrane which is undertaken using standard tympanotomy procedures as described above relative to the insertion of apparatus 10. Alternatively, insertion and placement of the apparatus 600 may be accomplished using a standard tympanomeatal flap procedure which likewise provides access to the middle ear and structures thereof. In addition, the apparatus 600 is preferably oriented so that at least a section of the primary stem portion 614 of the apparatus 600 extends through the incised tympanic membrane (or under the foregoing tympanomeatal flap), and resides within the external auditory canal of the patient.

Figure 15:
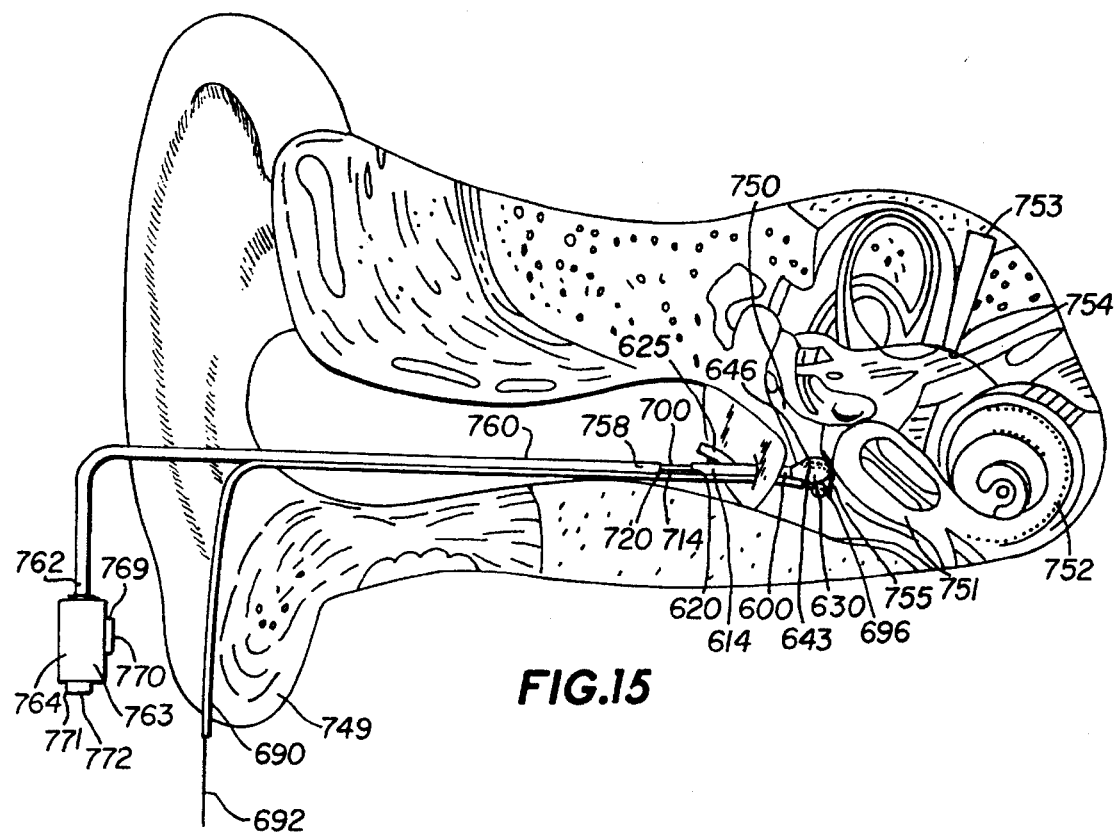
FIG. 15 is a schematic, partial cross-sectional view of the ear of a human subject illustrating the multi-component treatment system of FIG. 14 inserted therein.

FIG. 15 is a schematic, partial cross-sectional view of the ear 749 of a human subject illustrating the system 500 of FIGS. 13–14 inserted therein. As shown, the primary treatment apparatus 600 with the insert member 700 therein is positioned so that the reservoir portion 630 of the apparatus 600 is entirely within the middle ear, generally designated in FIG. 15 at reference number 750. The inner ear is generally designated in FIG. 15 at reference number 751, and further includes the cochlea 752, the endolymphatic sac 753, and the endolymphatic duct 754. The round window membrane is designated at reference number 755, and again constitutes an interface tissue structure between the middle ear 750 and the inner ear 751.

In FIG. 15, the reservoir portion 630 of the apparatus 600 is specifically positioned so that the fluid transfer means 643 is in direct physical contact with the round window membrane 755. Likewise, in order to transmit/receive electric potentials from the inner ear, the spherical member 696 on the proximal end 694 of the elongate conductive member 690 (e.g. wire 692) is positioned against and in direct contact with the round window membrane 755 in the middle ear 750. Prior to insertion of the apparatus 600 (and insert member 700) within the ear 749, the open first end 720 of the tubular portion 714 associated with the insert member 700 is operatively connected to the first end 758 of a tubular conduit 760 made of surgical grade plastic preferably using an adhesive composition known in the art (e.g. silastic cement) or by frictional engagement therewith. Connection of these components in this manner is facilitated by the fact that the tubular portion 714 of the insert member 700 is longer than the primary stem portion 614 of the apparatus 600. Therefore, the open first end 720 of the tubular portion 714 extends outwardly beyond the open first end 620 of the primary stem portion 614 as illustrated in FIG. 15. The conduit 760 further includes a second end 762 which is operatively connected to a fluid supply means 763 in the form of a source or supply 764 of fluid (e.g. water, air, or other liquids and gases). The supply 764 will include pump means 769 in the form of a conventional pressure pump unit 770 associated therewith, as well as temperature control means 771 in the form of a temperature control unit 772. In a preferred embodiment, if the supply 764 is designed to deliver water or other liquid materials, an exemplary supply 764 (and the above-described components associated therewith) will consist of a closed loop irrigation system of the type disclosed in Brookler, K. H., "Closed Loop Water Irrigator System", *Otolaryngol. Head Neck Surg.*, 87:364–365 (May–June 1979) which is incorporated herein by reference. This system is designed to deliver fluid to a balloon-type structure which is maintained at a temperature of about 28°–46° C. It is further discussed in U.S. Pat. No. 4,244,377 and is commercially available from Grams, Inc. of Costa Mesa, Calif. (USA). However, the present invention shall not be exclusively limited to this type of system. Any other type of fluid delivery and/or pressure/volume/temperature regulating system which is known in the art for the purposes set forth herein may also be employed.

Alternatively, if it is desired that the supply 764 of fluid deliver air or other gaseous materials, a system suitable for this purpose which includes the foregoing components is described in Densert, B., "Effects of Overpressure on Hearing Function in Meniere's Disease", *Acta Otolaryngol.* 103:32–42 (1987) and in U.S. Pat. No. 4,971,076. However, the present invention shall not be limited exclusively to the systems described in the foregoing references.

To operate the primary treatment apparatus 600 with the insert member 700 therein so that changes in the inner ear fluid, temperature, volume and/or pressure levels may be achieved, the supply 764 of fluid and the pump unit 770 are activated so that the selected fluid is delivered through the conduit 760 into the tubular portion 714 of the insert member 700, and into the fluid receiving portion 730 thereof. The fluid (e.g. air or water) is supplied at a pressure sufficient to cause expansion of the fluid receiving portion 730 which is able to occur due to the stretchable materials used to produce the insert member 700 as previously indicated. As the fluid receiving portion 730 expands, it pushes against the side wall 642 of the reservoir portion 630 in the apparatus 600 and ultimately causes the reservoir portion 630 to correspondingly expand in an outward direction. With respect to the applied fluid pressure, such pressure will need to be determined experimentally for each different patient based on the degree of fluid imbalance within the particular patient's inner ear fluid chambers. However, an exemplary liquid pressure range regarding the delivery of liquids from the supply 764 to the fluid receiving portion 730 of the insert member 700 will be about 0.2–200.0 mm H₂O which should cause the fluid receiving portion 730 and reservoir portion 630 to sufficiently expand as described above. An exemplary gas pressure range with respect to the delivery of gases from the supply 764 to the fluid receiving portion. 730 of the insert member 700 will be about 0.1–300.0 mm H₂O which should again cause the fluid receiving portion 730 and reservoir portion 630 to sufficiently expand. It should also be noted that the delivery of pressurized fluid from the supply 764 to the insert member 700 may be continuous (e.g. so that the fluid receiving portion 730 will remain in an expanded state for a selected period of time), or may be done in discrete rhythmic or arrhythmic pulses. In addition, if liquid medicine materials or other therapeutic agents are present within the internal cavity 638 of the primary treatment apparatus 600, the insert member 700 can be used to selectively force the liquid medicine materials or agents outwardly in an accelerated manner through the fluid transfer means 643 in the apparatus 600 as desired. This may be accomplished through the delivery of a selected fluid from the supply 764 to the insert member 700 in pulses at desired intervals.

Because the reservoir portion 630 of the apparatus 600 will ultimately be positioned directly adjacent to and against a selected middle-inner ear interface tissue structure (e.g. the round window membrane 755 as shown in FIG. 15), expansion of the reservoir portion 630 initiated by the insert member 700 will exert pressure on the selected interface tissue structure, with such pressure being transmitted to fluid materials within the inner ear 751. As a result, this procedure will correct fluid pressure imbalances within the inner ear on a temporary or permanent basis (depending on the extent of fluid pressure imbalance). In addition, the temperature control unit 772 associated with the source 764 of fluid may be used to heat or cool the liquids or gases prior to delivery thereof to the insert member 700. The delivery of heated or cooled fluids to the fluid receiving portion 730 will cause a corresponding increase or decrease in the temperature of the fluid receiving portion 730 which may then be conductively transmitted from the fluid receiving portion 730 to the reservoir portion 630 and into the inner ear 751 via the selected middle-inner ear interface tissue structure (e.g. the round window membrane 755). This situation will occur since the reservoir portion 630 is in direct physical contact with the round window membrane 75S as shown in FIG. 15. If heated fluids are delivered to the insert member 700, the inner ear fluids/fluid chambers will likewise experience an increase in temperature and therefore expand, causing the volume and pressure characteristics thereof to increase. The opposite result will be achieved if cooled fluid materials are delivered. Regarding the temperatures of the liquids or gases to be delivered to the insert member 700, the selected temperature levels will vary, depending on (1) the condition of the patient and extent of inner ear fluid imbalances; (2) the type of fluid being delivered to the insert member 700; and (3) the degree of pressure exerted by the expanded insert member 700 and reservoir portion 630 against the selected middle-inner ear interface tissue structure (e.g. the round window membrane 755). Liquid temperatures within a broad range of about 30°–44° C. are preferred, while gas temperatures within a broad range of about 20°–50° C. may be employed. However, such temperatures are provided for example purposes and the present invention shall not be limited to any particular temperature level as long as the selected temperature is not permanently and physically injurious to ear tissues (unless such effects are the goal of the particular treatment program being administered).

It should be noted that when the insert member 700 is in a deflated state, fluid materials may still be readily added to the reservoir portion 630 of the primary treatment apparatus 600 in the same general manner set forth above regarding the apparatus 10. Fluid addition is specifically accomplished through the open first end 626 of the secondary stem portion 625. The fluid is then able to pass through the passageway 624 in the primary stem portion 614 by virtue of the open zone 748 which exists between the deflated insert member 700 and the apparatus 600 as described above.

Finally, it should likewise be noted that the primary treatment apparatus 600 may be configured so that it does not include fluid transfer means (e.g. pores 646) therein. The system 500 using apparatus 600 without the fluid transfer means would nonetheless function in the same manner as described above, except that the system 500 would not be used to deliver fluid materials to the middle/inner ear.

The present invention represents a substantial advance in the art of middle and inner ear treatment. Use of the invention enables a wide variety of therapeutic procedures to be readily accomplished using a minimal number of physical components and minimally invasive surgical procedures. Specifically, the various embodiments of the invention set forth herein enable (1) the delivery of therapeutic agents to internal ear (e.g. inner ear) structures; (2) the withdrawal of fluid materials from the inner ear; (3) the inducement of temperature, pressure and volumetric changes in the fluids/fluid chambers of the inner ear; and (4) the electrophysiological monitoring of internal (e.g. inner) ear structures. Thus, the present invention and the structures/methods associated therewith represent a significant development with respect to the treatment of middle and inner ear problems.

Having herein described preferred embodiments of the present invention, it is anticipated that suitable modifications may be made thereto by individuals skilled in the art which nonetheless remain within the scope of the invention. For example, the present invention shall not be limited with respect to the construction materials being employed, the size thereof, the therapeutic agents being delivered, and the physiological environment in which the invention is used. The present invention shall therefore only be construed in accordance with the following claims:

The invention that is claimed is:

1. A treatment apparatus for delivering therapeutic agents into the inner ear of a human subject comprising:

a reservoir portion comprising an exterior wall and an internal cavity therein surrounded by said wall;

a tubular first stem portion comprising an open first end, a second end, and a passageway extending continuously through said first stem portion, said second end of said first stem portion being connected to said reservoir portion so that said passageway through said first stem portion is in fluid communication with said internal cavity in said reservoir portion; and a tubular second stem portion comprising an open first end, a second end, and a passageway extending continuously through said second stem portion, said second end of said second stem portion being connected to said reservoir portion so that said passageway through said second stem portion is in fluid communication with said internal cavity in said reservoir portion.

2. The treatment apparatus of claim 1 wherein said first stem portion is positioned on a first side of said reservoir portion and said second stem portion is positioned on a second side of said reservoir portion, said first side being directly opposite said second side so that said first stem portion and said second stem portion form a 180° angle relative to each other.

3. The treatment apparatus of claim 1 wherein at least one of said first stem portion and said second stem portion comprises a valve positioned therein.

4. The treatment apparatus of claim 1 wherein at least a portion of said apparatus is radiopaque so that said portion will be visible during application of X-rays thereto.

5. A treatment apparatus for delivering therapeutic agents into the inner ear of a human subject comprising:

a reservoir portion comprising an exterior wall and an internal cavity therein surrounded by said wall;

a tubular first stem portion comprising an open first end, a second end, and a passageway extending continuously through said first stem portion, said second end of said first stem portion being connected to said reservoir portion so that said passageway through said first stem portion is in fluid communication with said internal cavity in said reservoir portion;

a tubular second stem portion comprising an open first end, a second end, and a passageway extending continuously through said second stem portion, said second end of said second stem portion being connected to said reservoir portion so that said passageway through said second stem portion is in fluid communication with said internal cavity in said reservoir portion; and electrical potential transmission means fixedly secured to said apparatus for transmitting electrical potentials into and out of said inner ear.

6. The treatment apparatus of claim 5 wherein said electrical potential transmission means comprises an elongate conductive member, said conductive member comprising a proximal end and a distal end.

7. The treatment apparatus of claim 6 wherein said proximal end of said conductive member comprises a conductive spherical member fixedly secured thereto.

8. The treatment apparatus of claim 5 wherein said first stem portion is positioned on a first side of said reservoir portion and said second stem portion is positioned on a second side of said reservoir portion, said first side being directly opposite said second side so that said first stem portion and said second stem portion form a 180° angle relative to each other.

9. A method for delivering therapeutic agents to the inner ear of a human subject through the external auditory canal and middle ear thereof comprising the steps of:

providing a treatment apparatus comprising:
      a reservoir portion comprising an exterior wall and an internal cavity therein surrounded by said wall, said internal cavity comprising a supply of liquid therapeutic agents therein;
      a tubular first stem portion comprising an open first end, a second end, and a passageway extending continuously through said first stem portion, said second end of said first stem portion being connected to said reservoir portion so that said passageway through said first stem portion is in fluid communication with said internal cavity in said reservoir portion; and
      a tubular second stem portion comprising an open first end, a second end, and a passageway extending continuously through said second stem portion, said second end of said second stem portion being connected to said reservoir portion so that said passageway through said second stem portion is in fluid communication with said internal cavity in said reservoir portion;

forming an access port in said ear between said middle ear and said inner ear so that access to said inner ear from said middle ear may be achieved;

inserting said reservoir portion of said apparatus into said middle ear;

positioning said first end of said second stem portion within said external auditory canal at a position remotely spaced from said middle ear; and placing said first end of said first stem portion through said access port and within said inner ear so that said first end of said first stem portion is against and in direct contact with tissues of said inner ear to be treated by said apparatus, said liquid therapeutic agents within said reservoir portion being delivered from said internal cavity through said first stem portion to said tissues of said inner ear during said direct contact between said first end of said first stem portion and said tissues of said inner ear.

10. The method of claim 9 further comprising the step of delivering an additional supply of liquid therapeutic agents through said external auditory canal and into said first end of said second stem portion of said apparatus while said reservoir portion is maintained within said middle ear and said first end of said first stem portion is maintained within said inner ear.

11. A method for delivering therapeutic agents to the inner ear of a human subject through the external auditory canal and middle ear thereof comprising the steps of:

providing a treatment apparatus comprising:
      a reservoir portion comprising an exterior wall and an internal cavity therein surrounded by said wall, said internal cavity comprising a supply of liquid therapeutic agents therein;
      a tubular first stem portion comprising an open first end, a second end, and a passageway extending continuously through said first stem portion, said second end of said first stem portion being connected to said reservoir portion so that said passageway through said first stem portion is in fluid communication with said internal cavity in said reservoir portion;
      a tubular second stem portion comprising an open first end, a second end, and a passageway extending continuously through said second stem portion, said second end of said second[stem portion being connected to said reservoir portion so that said passageway through said second stem portion is in fluid communication with said internal cavity in said reservoir portion; and
      electrical potential transmission means fixedly secured to said apparatus for transmitting electrical potentials into and out of said inner ear, said electrical potential transmission means comprising an elongate conductive member, said conductive member comprising a proximal end and a distal end;

forming an access port in said ear between said middle ear and said inner ear so that access to said inner ear from said middle ear may be achieved;

inserting said reservoir portion of said apparatus into said middle ear;

positioning said first end of said second stem portion within said external auditory canal at a position remotely spaced from said middle ear;.

placing said first end of said first stem portion through said access port and within said inner ear so that said first end of said first stem portion is against and in direct contact with tissues of said inner ear to be treated by said apparatus, said liquid therapeutic agents within said reservoir portion being delivered from said internal cavity through said first stem portion to said tissues of said inner ear during said direct contact between said first end of said first stem portion and said tissues of said inner ear; and placing said proximal end of said conductive member in direct contact with tissues from at least one of said middle ear and said inner ear.

12. The method of claim 11 further comprising the step of delivering an additional supply of liquid therapeutic agents through said external auditory canal and into said first end of said second stem portion of said apparatus while said reservoir portion is maintained within said middle ear and said first end of said first stem portion is maintained within said inner ear.

* * * * *

UNITED STATES PATENT AND TRADEMARK OFFICE
CERTIFICATE OF CORRECTION

PATENT NO. : 5,476,446
DATED : December 19, 1995
INVENTOR(S) : Irving K. Arenberg It is certified that error appears in the above-identified patent and that said Letters Patent is hereby corrected as shown below:

Items [19] and [75],
On the Title Page in two places delete "Arenburg" and insert therefor "Arenberg".

Signed and Sealed this

Seventeenth Day of September, 1996

Attest:

BRUCE LEHMAN

Attesting Officer     Commissioner of Patents and Trademarks